(12) United States Patent
Weghorst et al.

(10) Patent No.: US 6,440,673 B1
(45) Date of Patent: *Aug. 27, 2002

(54) METHODS FOR IDENTIFYING NUCLEIC ACID MUTATIONS USING MISMATCH MODIFICATION

(75) Inventors: Christopher Mark Weghorst, Pickerington; Altaf Ahmad Wani, Columbus, both of OH (US)

(73) Assignee: Ohio State University, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/622,085

(22) PCT Filed: Feb. 12, 1999

(86) PCT No.: PCT/US99/03132

§ 371 (c)(1),
(2), (4) Date: Nov. 16, 2000

(87) PCT Pub. No.: WO99/41414

PCT Pub. Date: Aug. 19, 1999

Related U.S. Application Data

(63) Continuation-in-part of application No. 09/023,989, filed on Feb. 13, 1998, now Pat. No. 6,080,544.

(51) Int. Cl.[7] .......................... C12Q 1/68; C07H 21/02; C07H 21/04
(52) U.S. Cl. .......................... 435/6; 536/23.1; 536/24.3
(58) Field of Search .............................. 435/6; 535/23.1, 535/24.3; 935/76, 77, 78

(56) References Cited

U.S. PATENT DOCUMENTS

| 5,217,863 A | 6/1993 | Cotton et al. |
| 6,080,544 A | 6/2000 | Weghorst et al. |

FOREIGN PATENT DOCUMENTS

| WO | WO9204469 | 3/1992 |
| WO | WO9402517 | 2/1994 |
| WO | WO9507361 | 3/1995 |
| WO | WO9641192 | 12/1996 |

OTHER PUBLICATIONS

Chen et al., 1996, Carginogenesis 17:2603–2607.
Cotton et al., 1993, Mutation Res. 285:125–144.
Ganguly et al., 1989. Genomics 4: 530–538.
Ganguly et al., 1990, Nucleic Acids Res. 18: 3933–3939.
Hongyo et al., 1993, Nucleic Acids Res. 16:3637–3642.
Fountain et al., 1994 Proc. Natl. Acad. Sci. USA 89:10557–10561.
Keen et al., 1991 Trends Genet. 7:5.
Novack et al. 1986, Proc. Natl. Acad. Sci. USA 83:586–590.
Orita et al., 1989, Proc. Natl. Acad. Sci. USA 867:2766–2770.
Saiki et al., 1985, Science 230:1350.
Sheffield et al., 1989 Proc. Natl. Sci. USA 86:232–236.
The BRL Catalog pp. 22–23, (1985).
Tindall K. R. and Whitaker R.A., Environmental and Molecular Mutagenesis, vol. 18, 1991, pp. 23–1238.
Dolinnaya et al., 1981, Nucleic Acids Res. 19:879–895.
Wang et al., 1996 Carcinogenesis 17:2603–2607.
Wani et al., 1984 Photochem Photobiol. 40:465–471.
Wani et al., 1989, Nucleic Acid Res. 17:9957–9977.
Wani et al., 1991 Biochimica et Biophysica Acta 1088:259–269.
Zhou et al., 1996, Cancer Res. 37:582.
Wong et al., 1987, Nature 195:384–386.
Zhuang et al., 1991, Amer. J. Human Genet. 48:1186–1191.
Hongyo et al., 1993, Nucleic Acids Res. 21:3637–3642.
Wang et al., 1996 Carcinogeneis 17:625–630.

*Primary Examiner*—Ethan C. Whisenant
(74) *Attorney, Agent, or Firm*—McDonnell Boehnen Hulbert & Berghoff

(57) ABSTRACT

The present invention provides methods for specifically detecting DNA mismatches between heteroduplex strands produced between wildtype and mutation containing nucleic acid species. Kits for performing the methods of the invention are also provided.

32 Claims, 14 Drawing Sheets

Figure 1A. Heteroduplex Mismatches Recognized by CMC

| Wt | Potential Mutations | | | Heteroduplex Mismatches | | |
|---|---|---|---|---|---|---|
| | 1 | 2 | 3 | 1 | 2 | 3 |
| G···C | a···t | t···a | c···g | [G]···t / a···[C] | [G]···a / [t]···C | [G]···g / c···[C] |
| A···T | g···c | t···a | c···g | A···c / [g]···[T] | [A]···a / [t]···T | [A]···g / [c]···[T] |
| T···A | g···c | a···t | c···g | [T]···c / [g]···A | [T]···t / a···A | [T]···g / c···A |
| C···G | g···c | a···t | t···a | C···c / [g]···[G] | C···t / [a]···G | C···a / t···[G] |

□ = Modified by CMC

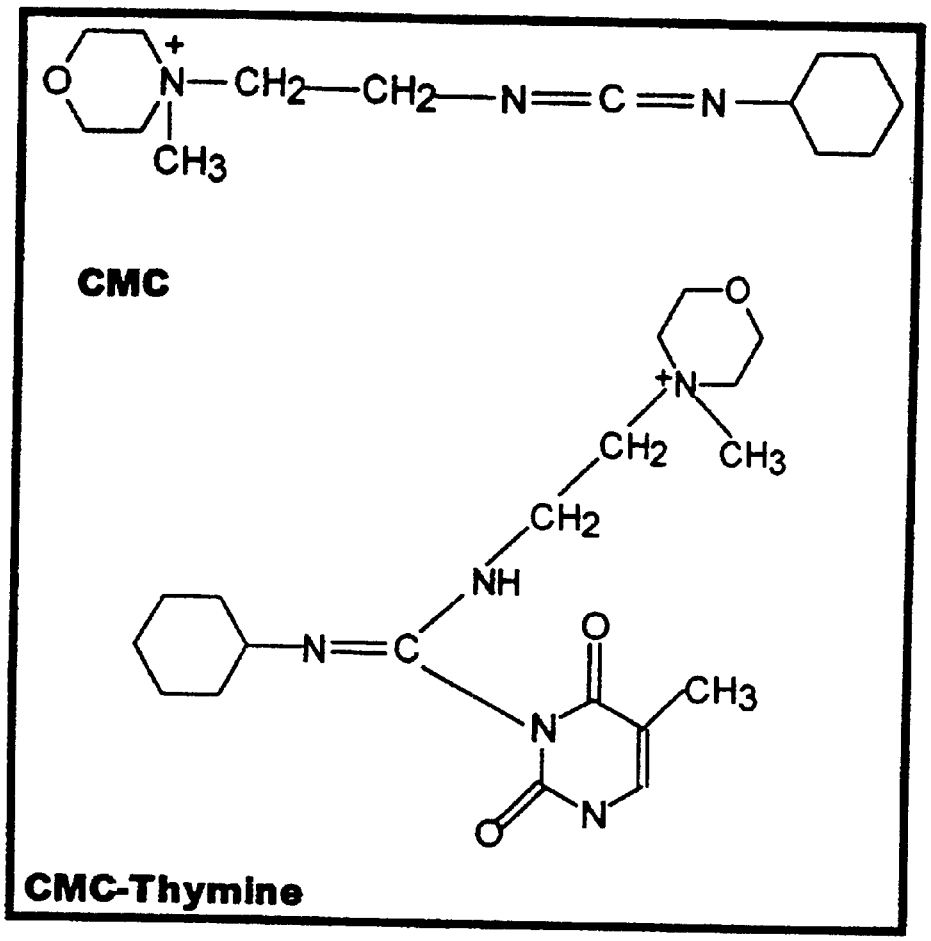
Figure 1B. Schematic representation of CMC modified thymine

Figure 2B. Experimental Design
Gene fragment with 18 bp deletion
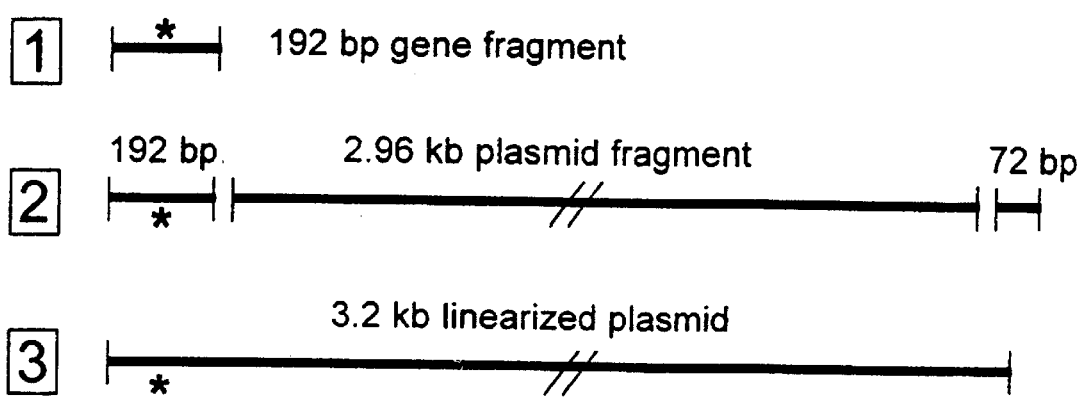
Gene fragment with 1 bp deletion
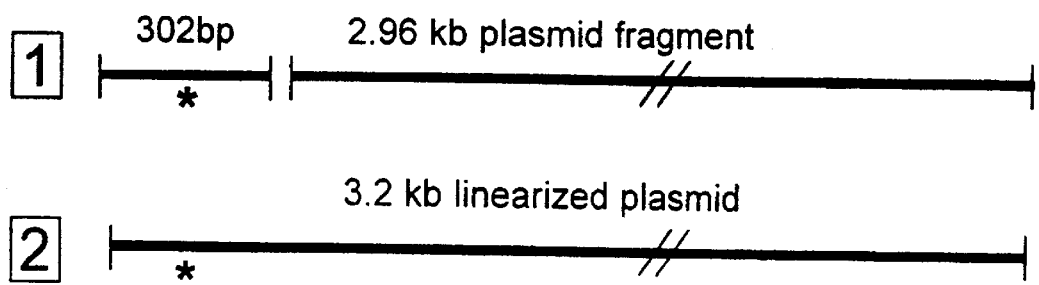

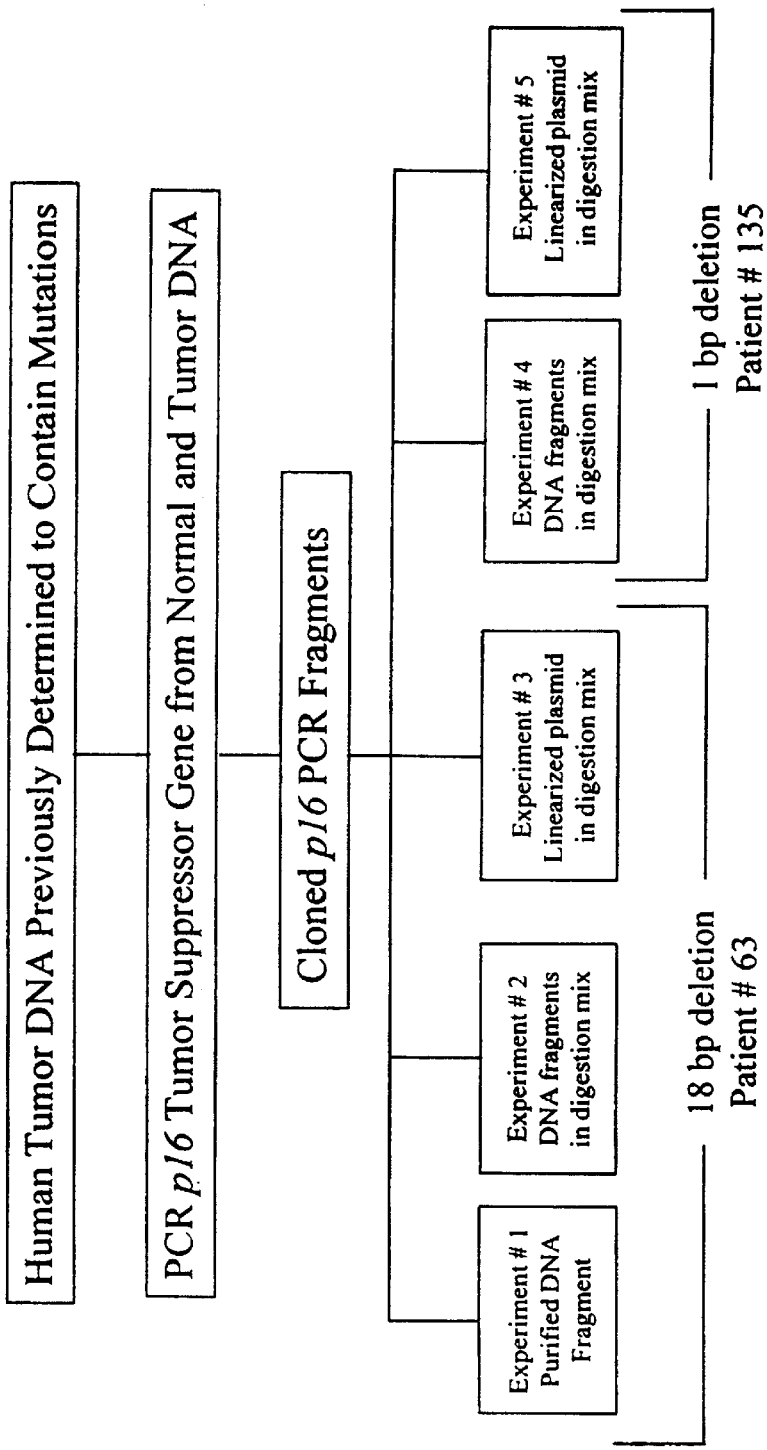
Figure 2C. Experimental Design

Figure 2D

Detection of Nucleotide Mismatches by CMC

Order of Treatment:

- Endonuclease digestion of DNA ⎫
- Heteroduplex formation          ⎬ Single Tube Protocol
- Exonuclease 1 treatment         ⎪
- CMC modification of mismatches ⎭

- Gel electrophoresis/immuno-blot ⎫ Detection
- ELISA plate reader              ⎭

Detection of Heteroduplex DNA by Immunoblotting 192 bp Fragment (18 bp deletion)

Detection of Heteroduplex DNA by Immunoblotting 2.96 kb Plasmid/72 bp Fragment/
192 bp Fragment(18 bp deletion)

3.2 kb DNA Fragment (18 bp deletion)

Detection of Heteroduplex DNA by Immunoblotting 2.96 kb Plasmid/302 bp Fragment (1 bp deletion)

Detection of Heteroduplex DNA by Immunoblotting 3.2 kb linearized plasmid (1 bp deletion)

SEQUENCE LISTING

<160> NUMBER OF SEQ ID NOS: 4

<210> SEQ ID NO 1
<211> LENGTH: 24
<212> TYPE: DNA
<213> ORGANISM: Homo sapiens

```
<400> SEQUENCE: 1
acaagcttcc tttccgtcat gccg                                          24

<210> SEQ ID NO 2
<211> LENGTH: 20
<212> TYPE: DNA
<213> ORGANISM: Homo sapiens

<400> SEQUENCE: 2
ccaggcatcg cgcacgtcca                                               20

<210> SEQ ID NO 3
<211> LENGTH: 20
<212> TYPE: DNA
<213> ORGANISM: Homo sapiens

<400> SEQUENCE: 3
ttcctggaca cgctggtggt                                               20

<210> SEQ ID NO 4
<211> LENGTH: 22
<212> TYPE: DNA
<213> ORGANISM: Homo sapiens

<400> SEQUENCE: 4
tctgagcttt ggaagctctc ag                                            22
```

METHODS FOR IDENTIFYING NUCLEIC ACID MUTATIONS USING MISMATCH MODIFICATION

This application is a U.S. national phase application pursuant to 35 U.S.C. §371 of International Application, No. PCT/US99/03132, filed Feb. 12, 1999, which is a continuation-in-part of U.S. patent application Ser. No. 09/023,989, filed Feb. 13, 1998, now U.S. Pat. No. 6,080,544

BACKGROUND OF THE INVENTION

1. Field of the Invention

The invention provides methods for distinctly detecting basepair mismatches between heteroduplex strands produced between wildtype and mutation-containing nucleic acid species. Specifically, this invention relates to methods for detecting nucleotide sequence polymorphisms including mutations in genes of biological organisms, including humans, for disease diagnosis and other purposes. More particularly, the invention relates to methods for detecting disease-related genetic polymorphisms for clinically relevant purposes, as well as providing a basic research tool for detecting genetic polymorphisms, mutations and mismatches between nucleic acid heteroduplex strands in nucleic acids of all nucleic acid-based life forms. The methods of the invention involve chemically modifying mismatched sites in such heteroduplexes and detecting the sites of chemical modification. Applications of the methods of the invention for disease detection, intervention and monitoring are also provided.

2. Background of the Related Art

In the genetic and medical arts, the existence of genetic polymorphism is frequently associated with differences between the most common species (the wildtype allele) at a genetic locus and alternative forms (the polymorphisms). When such genetic polymorphism is associated with deleterious consequences such as disease, it is frequently termed a mutation. Mutations associated with disease have been established for a number of diseases.

Genetic mutation is frequently detected in cancer, and is also the basis of profound heritable and somatic cell diseases. It is generally recognized that cancer is a multistage process involving the accumulation of mutations and other genetic alterations in a pre-neoplastic cell. The rapid and reliable detection of such altered states of nucleic acids is tantamount to defining the most significant steps of development of the resulting tumors, and has important implications for developing appropriate therapies therefor. Specifically, these mutations occur in particular growth- and differentiation-regulatory genes in eukaryotic cells, termed oncogenes and tumor suppressor genes, that are the targets for genetic lesions caused by carcinogenic chemicals, radiation and other cancer-causing substances and processes.

One of the most common types of genetic alteration in oncogenes and tumor suppressor genes is a single nucleotide substitution, termed a "point mutation." Such point mutations typically occur against a background of the entirety of the rest of the nucleotide sequence encoding the oncogene or tumor suppressor gene. There is therefore a need in the art for the development of rapid, reliable and sensitive methods for detecting point mutations in nucleic acids (e.g., oncogenes, genetically heritable diseases) or nucleic acid changes in somatic cells, or any sequence alterations in DNA or RNA, whether wild-type DNA or DNA, or purely synthetic DNA or RNA. The method disclosed herein fulfills a critical need in the art, and is generally useful in detection, definition and diagnosis of disease. When contrasted with the current state of technology, this method accelerates the field of disease mutation discovery, with the potential of improving drug discovery for the mitigation of these diseases.

A variety of methods for detecting mutations in DNA are known in the prior art. These include direct sequencing of mutant DNA (Wong et al., 1987, Nature 195: 384–386); allele-specific oligonucleotide hybridization (Wallace et al., 1981, Nucleic Acids Res. 19: 879–895); single-strand conformation polymorphism (Orita et al., 1989, Proc. Natl. Acad. Sci. USA 86: 2766–2770); denaturing gradient gel electrophoresis (Sheffield et al., 1989, Proc. Natl. Acad. Sci. USA 86: 232–236); heteroduplex analysis (Keen et al., 1991, Trends Genet. 7: 5); and chemical (Cotton et al., 1988, Proc. Natl. Acad. Sci. USA 85: 4397–4401) or enzymatic (Youil et al., 1995, Proc. Natl. Acad. Sci. USA 92: 87–91) cleavage of mismatches. Each of these methods has serious drawbacks that preclude its use as a rapid, reliable and sensitive method for nucleic acid mismatch detection. The state of this art has recently been reviewed by Cotton (1993, Mutation Res. 285: 125–144).

The use of chemical modification of mismatches has been attempted in the prior art.

Novack et al., 1986, Proc. Natl. Acad. Sci. USA 83: 586–590 disclosed detection of a single basepair mismatch in DNA by chemical modification and gel electrophoresis.

Wani et al., 1989, Nucleic Acids Res. 17: 9957–9977 disclose immunoassays for carbodiimide-modified DNA.

Ganguly et al., 1989, Genomics 4: 530–538 disclose the use of electron microscopic methods for detecting chemically modified DNA mismatches.

Ganguly et al., 1990, Nucleic Acids Res. 18: 3933–3939 teach the use of primer extension and polymerase chain reaction to detect chemically modified DNA mismatches.

Wani et al., 1991, Biochimica et Biophysica Acta 1088: 259–269 disclose analysis of carbodiimide-modified DNA using specific antibodies as immunochemical reagents.

Zhuang et al., 1991, Amer. J. Human Genet. 48: 1186–1191 demonstrate detection of a single base mutation in a human collagen gene using direct sequencing of polymerase chain reaction-amplified, chemically modified heteroduplex DNA.

While each of these reports discloses some aspect of chemical modification of DNA to detect heteroduplexes, the prior art is devoid of teachings or disclosure of an assay having the necessary sensitivity and reliability required for routine clinical use. Moreover, the prior art, or any combination thereof, teaches only basic research applications of the technology, with the findings of these studies explicitly referenced as being "interesting."

There remains a need in the art for rapid, reliable and sensitive methods for detecting mismatches between wildtype and disease-related mutant nucleic acids, to provide genetic, clinical and other relevant (e.g., diagnostic) information for research, diagnosis and therapy.

SUMMARY OF THE INVENTION

The present invention provides methods for specifically detecting basepair mismatches between heteroduplex strands produced between reference (wildtype) and altered (mutant) nucleic acid species. The invention provides methods for chemically modifying mismatched sites in such heteroduplexes and detecting the sites of chemical modification. In preferred embodiments, chemical modification is produced using a water-soluble, single-strand DNA-specific reagent, N-cyclohexyl-N'-(4-methylmorpholinium)-ethylcarbodiimide (CMC). In alternative preferred embodiments, the chemical mismatch modifying agent is detectably-labeled. In certain of these embodiments, the chemical mismatch modifying agent is provided in a "masked" state, wherein the detectable label is only detected when the chemical mismatch modifying agent is covalently linked to the site of heteroduplex mismatch. In additional alternative preferred embodiments, the chemical mismatch modifying agent further comprises a masked beacon molecule, which is unmasked upon formation of mismatch modification by the agent.

In preferred embodiments, sites of chemical mismatch modification are detected immunochemically using specific antibodies, preferably comprising polyclonal antisera and most preferably monoclonal antibodies. In alternative preferred embodiments, said antibodies are chemically linked to aggregation or accumulation agents, such as magnetic or iron beads or antigenic haptens such as biotin, to permit accumulation or aggregation of the antibodies after recognition of a chemically-modified, mismatched heteroduplex.

Kits are also provided for modifying heteroduplex nucleic acid, including reagents, buffers, single stranded nucleic acid modifying agents and enzymes such as exonuclease as described herein. Kits are also provided for detecting chemically modified heteroduplex nucleic acid, including reagents, buffers, specificity reagents such as primary and secondary antibodies, and detection reagents such as colorimetric detection reagents. Combination kits for modifying and detecting said modified heteroduplex nucleic acid are also provided by the invention.

Specific preferred embodiments of the present invention will become evident from the following more detailed description of certain preferred embodiments and the claims.

BRIEF DESCRIPTION OF THE DRAWINGS

FIG. 1A is a schematic diagram of heteroduplex mismatches recognized by CMC modification, and FIG. 1B is a schematic illustration of DNA base modification using CMC.

FIG. 2B is a diagram of the DNA fragments used to produce heteroduplexes as described in Examples 1 and 2, FIG. 2C depicts the experimental protocol for the experiments described in Examples 1 and 2, and FIG. 2D illustrates the experimental protocol.

DETAILED DESCRIPTION OF THE PREFERRED EMBODIMENTS

For the purpose of this application, the abbreviation "CMC" is intended to represent N-cyclohexyl-N'-(4-methylmorpholinium)-ethylcarbodiimide.

The present invention provides sensitive and specific methods for mismatch detection in nucleic acid heteroduplexes. These methods provide a rapid, reliable, sensitive and specific set of assays for detecting and identifying mutations; applications include, but are not limited to, genetic-based diseases and genetic variations (polymorphisms) in humans and other animals, as well as plants and microorganisms. Preferably, the methods of the invention are useful for detecting genetic mutation related to animal, preferably human, disease, and most preferably neoplastic disease.

The chemical basis of CMC-mediated mismatch detection is illustrated in FIG. 1A. For each wildtype basepair, the potential nucleotide substitutions are shown, followed by the heteroduplex mismatches expected upon hybridization of a wildtype strand with each of the potential base pair substitutions. It can be seen that for each case, at least one of the resulting heteroduplexes will be modified by treatment with CMC. Thus, every possible substitution event is subject to modification by CMC and detection using CMC-specific reagents.

CMC is known to react specifically with imino groups at the nitrogen 3 (N3) position of thymidine and uracil, and at the N1 position of guanine. These sites are freely available in most RNA species, and in single-stranded DNA. Reactivity of CMC with these molecules is consequently very high. On the other hand, these sites in the nucleotide bases are not available in double-stranded DNA, since they are involved in hydrogen bonding of the duplex. Therefore, CMC is unable to react with native, double-stranded DNA to any detectable extent.

Variants of normal duplex DNA structure, containing small, single base or relatively large single-stranded regions, are able to be modified by CMC treatment. Such variants include mismatches in base pairing caused by annealing of wildtype and mutant DNA strands to form heteroduplexes. Although there is some hydrogen bonding between even mismatched basepairs, the N3 nitrogen of thymidine and the N1 nitrogen of guanine are accessible to the CMC reagent. Other chemicals that are known to react with DNA bases in single-stranded DNA (e.g., osmium tetroxide, hydroxylamine, etc.) or those yet to be identified are also expected to be capable of modifying mismatched DNA. An illustration of CMC modified thymidine (at N1) is shown in FIG. 1B; a similar reaction occurs with guanine at the N1 position.

Figure 9A:
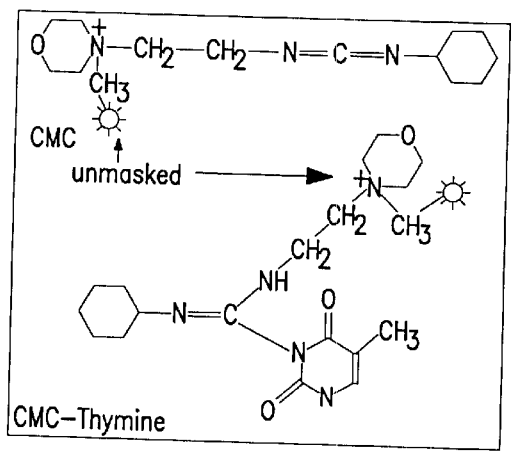
FIGS. 9A through 9C illustrate different embodiments of the detectably-labeled chemical mismatch modifying agent CMC of the invention.
Figure 9B:
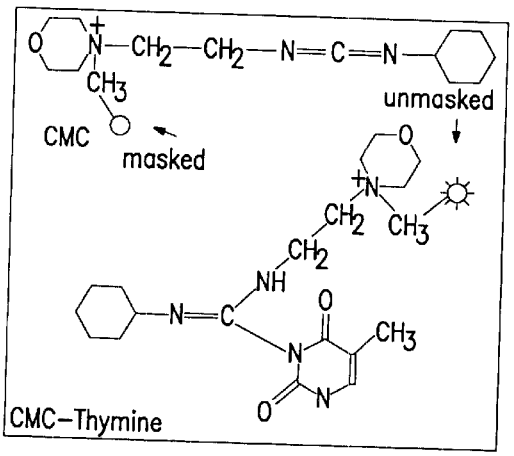
Figure 9C:
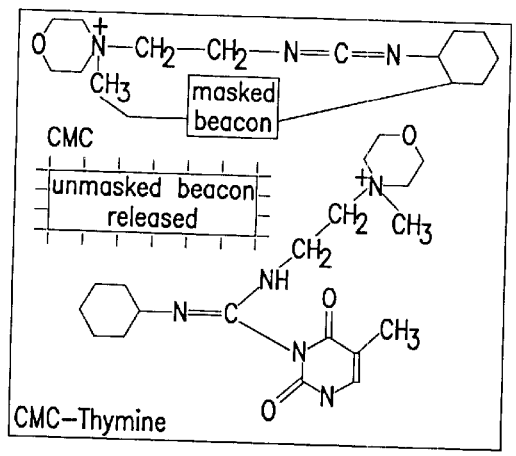

Alternative forms of CMC or other chemical mismatch heteroduplex modifying agents are also useful in the practice of the methods of this invention. For example, detectably-labeled species of such agents provides a means to detect and quantify the extent of DNA labeling (e.g., by association of the detectable label with the DNA as detected e.g. by acid-precipitable radioactivity for radiolabeled species). Detectably-labeled agents also increase the sensitivity of detection of mismatched heteroduplex DNA. The use of detectably-labeled chemical mismatch heteroduplex modifying agents can in certain embodiments of the methods of the invention be specific for and provide the sole means for detecting the mismatch, using well-characterized mutations at specific polymorphic sites. Alternatively, the detectable label can be used in conjunction with the other mismatch detection means provided by the invention, further increasing the detection sensitivity of those reagents. An example of such a detectably-labeled species of CMC is shown in FIG. 9A. Detectable labels useful in this aspect of the invention include but are not limited to radioactive isotopes ($^3$H, $^{14}$C, $^{32}$P, or $^{35}$S) and labeling moieties (such as phosphates), fluorescent or chemiluminescent labels, antigenic or hapten labels (such as biotin), and enzymatic labels (such as alkaline phosphatase or horse radish peroxidase). In other embodiments, the detectable label is "masked," typically by the presence of a stable protecting group that prevents detection of the label, and that is removed, typically by chemical treatment, upon binding of the chemical mismatch heteroduplex modifying agent to mismatched heteroduplex DNA. An example of such a "masked" detectably-labeled species of CMC is shown in FIG. 9B. In yet additional embodiments, the detectable label is a "beacon" molecule, most preferably a masked beacon molecule, that is released from and becomes detectable upon binding of the chemical mismatch heteroduplex modifying agent to mismatched heteroduplex DNA (as is described in Science 279: 1228–1229, 1998). An example of such a "beacon"-labeled species of CMC is shown in FIG. 9C.

The methods of the invention are used to detect heteroduplex mismatches between wildtype and mutant-containing DNA. As an example, a general schematic outline of the inventive methods is provided in FIG. 2A. In the Figure is shown two DNA molecules, one wildtype at a sequence and the other containing a mutation indicated by paired asterisks. DNA fragments containing the wildtype and mutated sequences are isolated, denatured and rehybridized to form three types of molecules: a wildtype homoduplex, a mutant homoduplex and heteroduplexes between one strand of the wildtype fragment and one strand of the mutant fragment. It will be recognized that there will be two species of heteroduplex formed, comprising the "Watson" strand of one DNA fragment hybridized with the "Crick" strand of the other DNA fragment, and vice versa. The expected mismatches in the heteroduplexes are as shown in FIG. 1.

Figure 2A:
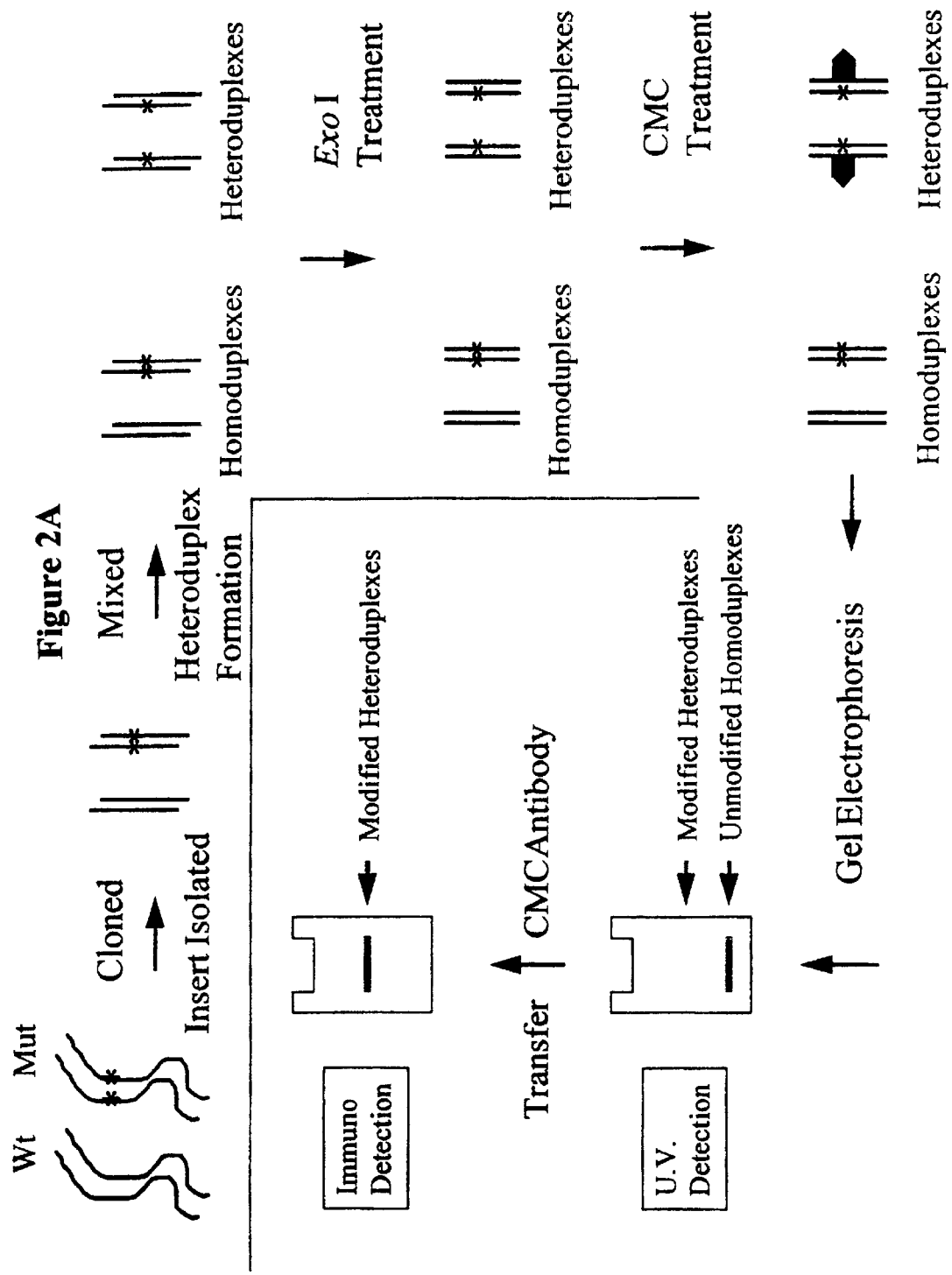
FIG. 2A is a diagram of the methods of the invention.

Also illustrated in FIG. 2A is the expected result that the heteroduplexes will form at least in part imperfectly, leaving single stranded DNA available for hairpin and other non-specific hybridization that is expected to produce artifactual mismatches. Also expected (but not explicitly shown in FIG. 2A) is unhybridized single stranded DNA, since most heteroduplex hybridizations will be performed under conditions intended to maximize the production of wildtype:mutant heteroduplexes and minimize mutant homoduplex formation (which is an uninformative event). Both of these types of excess single stranded DNA are expected to produce artifactual mismatches that would be recognized and modified by CMC and produce spurious results. In order to avoid this, an exonuclease treatment step is included in the preferred embodiment of the methods of the invention, as shown in FIG. 2A. The usefulness of the exonuclease digestion in producing specific CMC modification and mismatch detection is shown below in the Examples.

After exonuclease treatment, the heteroduplex-containing reaction mixture is suitable for CMC modification. As shown in FIG. 2A, this treatment leaves the wildtype and mutant homoduplexes unmodified, since these species are completely homologous and are expected to form stable double helices at appropriate temperatures below the melting temperature of the homoduplex. Heteroduplexes, on the other hand, are modified at one or the other or both of the mismatched nucleotide residues; as shown in FIG. 1, either or both of the mismatched species are available to be chemically modified, depending on the nature of the mismatch.

CMC modification should be performed at the appropriate temperature, which is determined empirically for each heteroduplex. Generally, the appropriate temperature is a temperature at which the CMC modification reaction proceeds optimally while avoiding denaturation of perfectly-matched nucleotide basepairs, which can then be artifactually CMC modified under some conditions. This temperature range is from about 20°–75° C., more preferably from about 35° C.–55° C., and most preferably from about 40° C.–50° C.

After formation of the CMC modified heteroduplexes, the species are typically separated to distinguish between homoduplex and heteroduplex formation. This separation also enables detection of spurious homoduplex labeling due to inappropriate choice of reaction conditions, and minimizes the likelihood of confusing true heteroduplex mismatches with artifactual homoduplex mismatches, since the heteroduplexes are expected to be separated from the homoduplexes using most conventional separation techniques. Separation can advantageously be performed by any separation method known in the art, and most preferably is performed using gel electrophoresis, using agarose or acrylamide gels and buffer systems appropriate for the size of the fragments to be separated and resolved. Both DNA homoduplexes and heteroduplexes are typically visualized after electrophoretic separations using a non-specific stain such as ethidium bromide, and the DNA then transferred to a solid support such as nitrocellulose or other membranes (typically by "Southern" blotting) for detection of CMC-modified heteroduplexes. CMC-modified heteroduplexes are detected using a CMC-specific antibody conjugated to a detection moiety, by immunochemical staining of a primary CMC-specific antibody bound to the heteroduplex using a detectably-labeled secondary antibody. The position and extent of CMC modification is developed according to the needs of the assay: maximum sensitivity conditions are used to detect rare or under-represented heteroduplex mismatches in a DNA fragment population, while stringent sensitivity conditions are used to make comparisons between samples containing relatively abundant amounts of DNA mismatches.

Figure 8:
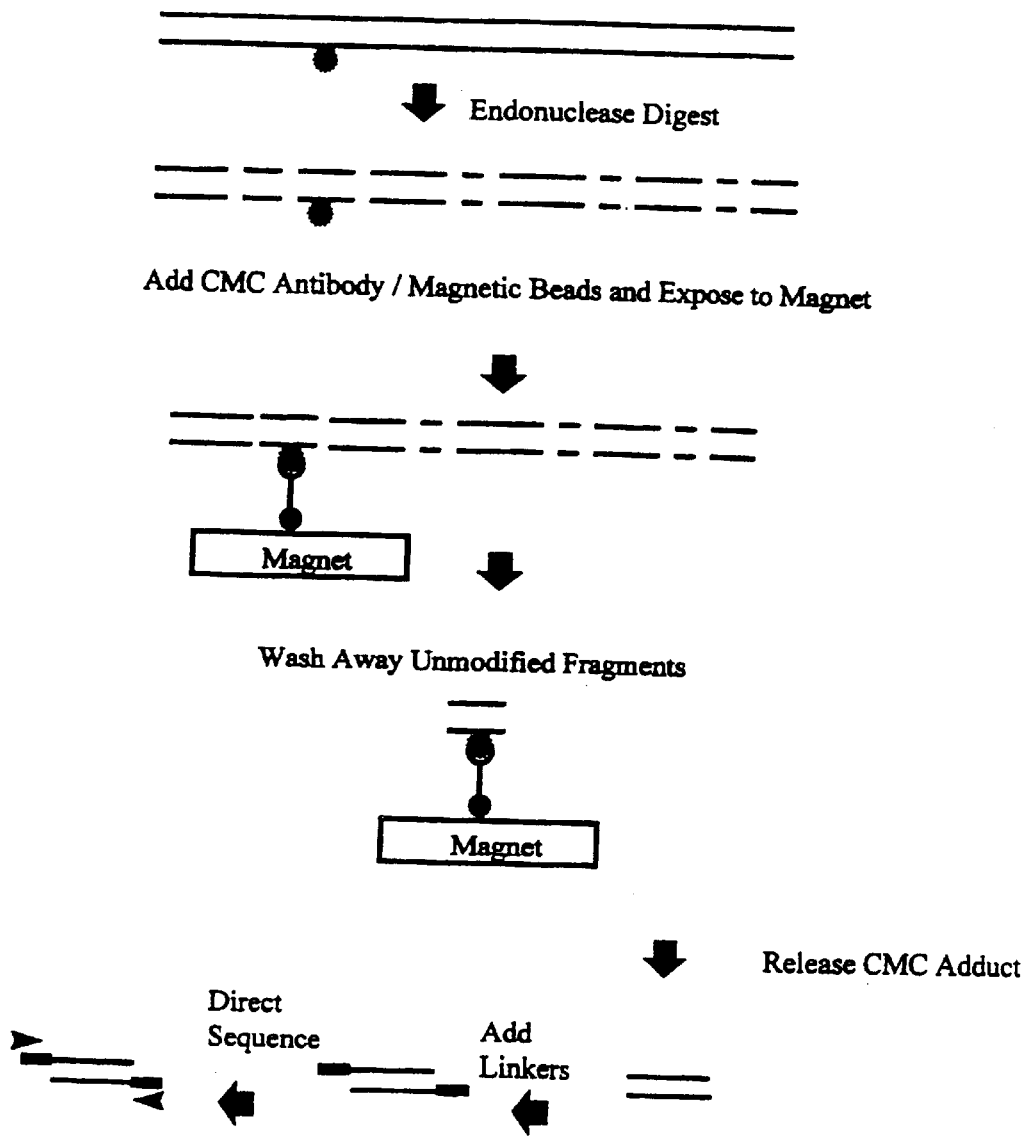
FIG. 8 is a schematic diagram of an embodiment of the invention whereby ferritin-conjugated anti-CMC antibodies are collected using a strong magnet and isolated from non-mismatch containing restriction enzyme digestion fragments. Release of the segregated restriction fragment containing the mismatch permits cloning, sequencing and other routine molecular biological manipulations without using convention separation techniques.

In an alternative embodiment, the existence of the mismatch is used to isolate a DNA fragment containing the mismatched heteroduplex from a DNA sample, wherein most preferably the fragment is a restriction enzyme digestion fragment. In this embodiment, an antibody specific for the chemical mismatched heteroduplex modifying agent is chemically linked to an aggregation or accumulation agent that permits accumulation, capture or aggregation of a modified mismatch heteroduplex fragment. In preferred embodiments, the aggregation or accumulation agent is a magnetic or iron bead that can be separated from non-labeled fragments using a strong magnet; or an antigen or hapten such as biotin, that permits capture of the modified mismatch heteroduplex-containing DNA fragment using, e.g., avidin or streptavidin; or a chemically-inert bead or particle that permits accumulation of the modified mismatch heteroduplex-containing DNA fragment using, e.g., centrifugation. A schematic diagram of this embodiment of the methods of the invention is shown in FIG. 8. The isolated, modified mismatch heteroduplex-containing fragment can be used for cloning, sequencing and other molecular biological techniques after release of the chemical mismatch heteroduplex modifying agent from the fragment.

In the practice of the methods of the invention, the wildtype and mutant nucleic acid will be understood to include genomic DNA, reverse-transcribed complementary DNA (cDNA), or RNA. Cloned DNA species, and in vitro amplified species, derived from genomic DNA, cDNA or RNA are also within the scope of the methods of the invention. The only requirement for being used as a source of nucleic acid for analysis is that there be available both wildtype and mutant DNA for preparing heteroduplexes. Paired DNAs can be derived from matched normal and mutant tissue samples, for example, normal and neoplastic tissues, or can be provided using mixed nucleic acid sources, such as most neoplastic tissues. Such mixed tissues are particularly useful when the embodiment of the methods of the invention includes the step of isolating and purifying DNA fragments comprising the wildtype and mutant species.

In preferred embodiments, DNA fragments derived from wildtype and mutant nucleic acids are produced using any or a variety of in vivo or in vitro amplification reactions, including but not limited to polymerase chain reaction (a preferred embodiment), ligase chain reaction, branched DNA signal amplification, boomerang DNA amplification, Q-beta replication, transcription-based amplification, isothermal nucleic acid sequence based amplification, self-sustained sequence replication assay, strand displacement activation, cycling probe technology, recombinant DNA ("cloning") and combinations or variations thereof.

In the practice of the invention, the nucleic acid or derived fragments thereof must contain at least one basepair mismatch in order to form a detectable heteroduplex. In addition, multiplex embodiments of the invention are provided, wherein separable heteroduplexes are produced for more than one gene or more than one mutation in the same gene.

Modification of heteroduplex mismatches is achieved most preferably by chemical modification using N-cyclohexyl-N'-(4-methylmorpholinium)-ethylcarbodiimide (CMC). Alternatively, heteroduplex mismatches can be modified using other chemical DNA modifying agents, including but not limited to osmium tetroxide, hydroxylamine, or Mut S protein, using reagent-specific modifications of the methods using CMC. Chemically-modified DNA is detected most preferably using immunochemical reagents that specifically recognize the modified DNA. Preferred reagents include antibodies, including antisera, preferably polyclonal antibodies and most preferably monoclonal antibodies and hybridomas producing such antibodies.

Immunochemical detection of chemically modified DNA mismatches is optimally performed using a detectable moiety conjugated to the immunochemical reagent. In preferred embodiments, the detection moiety includes radioactive and non-radioactive moieties. Radioactive detection moieties include conventionally useful radioisotopes, including $^3$H, $^{14}$C, $^{32}$P, $^{35}$S, $^{123}$I, $^{125}$I, $^{131}$I, $^{99m}$Tc, or other useful radioisotopes. Non-radioactive detection moieties include, but are not limited to, colorimetric, fluorescent, and chemiluminescent moieties, and ferromagnetic particles or latex beads.

Detection methods useful in the practice of the invention include enzyme-linked immunosorbent assay (ELISA), radioimmunoassay (RIA) and immunoblot methods. In preferred embodiments, immunochemical reagents specific for chemically modified mismatches are conjugated with enzymes such as alkaline phosphatase or horse radish peroxidase and immunochemical recognition of mismatches detected by the production of a colored product. Alternatively, and also preferred, secondary immunochemical reagents, preferably antibodies, specific for the immunochemical reagents used to specifically detect the mismatch, preferably an antibody, more preferably a polyclonal antisera and most preferably a monoclonal antibody, are used in so-called "sandwich assays" to detect chemically modified mismatches in heteroduplex DNA by binding of the detectably-labeled secondary antibody to a primary antibody specific for chemically modified heteroduplex DNA. CMC-specific antibodies are prepared as polyclonal antisera using methods well-understood in the art, as illustrated by the teachings of Wani et al., 1984, *Photochem. Photobiol.* 40: 465–471; Wani et al., 1989, *Nucleic Acids Res.* 17: 9957–9977; and Wani & Yamasaki, 1991, *Biochem Bioiphys Acta* 1088: 259–269.

In especially preferred embodiments of the methods of the invention, the modified mismatch heteroduplex-containing fragments can be detected using the following modification of the conventional enzyme-linked immunosorbent assay (ELISA). In this embodiment, the modified mismatch heteroduplex-containing nucleic acid fragments are produced as described herein. An amount of the fragments, optionally along with the remainder of the modified and unmodified fragments in a nucleic acid sample, are transferred and immobilized to a conventional ELISA array, such as a 96-well microtitre dish. The immobilized nucleic acid fragments are then incubated with an antibody that specifically recognizes the chemical mismatched heteroduplex modifying agent. In certain embodiments, this antibody is detectably labeled, most preferably with an enzyme such as alkaline phosphatase or horse radish peroxidase that can produce an easily-detectable product. In preferred embodiments, the first or primary antibody-antigen complex in the wells of the microtitre dish is further incubated with a secondary antibody specific for the first antibody, wherein the second antibody is linked to the enzyme or other detectable label. In all embodiments, the amount of the detectable product is related to nucleic acid fragment concentration as in conventional ELISA assays.

Results obtained using the methods of the invention are dependent in part on reaction conditions for heteroduplex formation CMC modification and chemically modified mismatch detection. In the practice of the invention, certain of these reaction conditions will vary depending on the extent and nature of the mismatch(es), the size and complexity of the nucleic acid fragments, and the chemical species forming the heteroduplex (DNA:DNA, DNA:RNA or RNA:RNA), and therefore must be determined empirically as described herein. Such conditions include temperature (preferably, from about 20° C. to about 75° C.), ionic strength (preferably, from about 50 mM to about 500 mM NaCl), incubation time (preferably, from about 1 to about 15 h), and conditions such as buffer compositions and the presence of helix stabilizing or destabilizing agents, such as formamide, glyoxal, methyl mercury hydroxide, dextran sulfate, and others known to those of skill in the art. Determination of these empirical conditions is well within the skill of one of ordinary skill in the art, in view of the explicit teachings of the instant specification and the knowledge in the art.

Restriction enzymes, exonucleases, polymerases and other molecular biological reagents used in the practice of the invention as disclosed herein are used according to the manufacturer's instructions and according to the conventional teachings of the art. For eliminating excess single stranded DNA from heteroduplex reaction mixtures (particularly under conditions wherein an excess of the wildtype strands are provided to maximize production of heteroduplexes), exonuclease digestion is a preferred embodiment. Alternatively, such single stranded DNA can be removed using hydroxylapatite and other affinity matrices, or chromatographic methods that are exclusionary for single stranded nucleic acid. In another alternative, DNA:RNA heteroduplexes can be purified from excess RNA using RNases.

In preferred embodiments, the reactions performed according to the methods of the invention are advantageously performed in a single reaction vessel or tube. Specifically, as shown schematically in FIG. 2D, DNA digestion with endonuclease, heteroduplex formation, exonuclease treatment, and chemical (preferably, CMC) modification of mismatches is performed in a single reaction tube, wherein the buffer conditions are chosen to facilitate successful completion of each of the individual chemical reaction steps. This embodiment is advantageous because it permits the nucleic acid to be subjected to the individual reaction steps of the protocol without intervening purification steps that can reduce signal yield, economic application, and otherwise tend to produce aberrant, suboptimal or unusable results. This embodiment has the further advantages of being convenient, permitting both rapid processing, high throughput and the capacity to be automated, and improved reproducibility.

Nucleic acid separation methods useful in the practice of the invention include gel electrophoresis (a preferred embodiment), including both agarose and polyacrylamide gels. In the practice of the invention using gel electrophoretic methods, separated heteroduplex DNA is most preferably transferred to a solid support, such as a nylon or nitrocellulose filter, for immunochemical or other detection of chemically modified mismatches. Capillary electrophoresis is also advantageously used to separate homo- and heteroduplexes. Heteroduplexes can also be specifically enriched in a population of homo- and heteroduplexes using hybridization to sequence tags provided, for example, at the ends of amplification primers. Alternatively, ferromagnetic particles or beads can be used to isolate DNA molecules consisting of at least one strand of a mutation-containing DNA fragment, under conditions where mutant homoduplex formation is disfavored.

The methods of the invention are useful for any pair of mutant and wildtype nucleic acids wherein heteroduplexes can be prepared. Non-limiting examples of uses for the methods of the invention include detection of disease-related mutations, including genetic diseases, diseases related to inherited or inborn errors of metabolism, other inherited disorders such as cystic fibrosis, Huntington's disease, muscular dystrophy, hemophilia, thalassemia, sickle cell anemia, neurofibromatosis and all malignancies. Other useful applications of the methods of the invention include screening and detection of the products of in vitro mutagenesis, identification of new disease genes, identification of new genetic markers such as mini- or microsatellite DNA, or polymorphisms such as restriction fragment linked polymorphisms (RFLP). The methods of the invention are also useful in basic medical research, including identification of sequence information and mutations using human nucleic acid sequences obtained, for example, from the efforts of the Human Genome Project; measurement of polymorphisms in humans at newly-isolated genetic loci; the establishment of genetic markers comprising DNA sequence polymorphisms, which is in turn useful for developing physical and genetic maps of chromosomal DNA; population studies, for establishing strain or group genetic markers, including genetic markers associated with human races or ethnic groups, and thus for anthropological and forensic purposes. These characterizations can be suitably applied to plants, animals including humans, and microorganisms (including viruses).

In addition, the methods of the invention are applicable to the development of non-radioactive nucleic acid labeling techniques, in combination, for example, with chemiluminescence detection methods. In such embodiments, chemically modified nucleic acid is useful for probing nucleic acid sequences using established techniques such as Southern and "Northern" blotting methods.

The following Examples illustrate but do not limit the methods of the invention. FIG. 2B is a schematic diagram of the Experimental Design of the experiments described in the Examples. Human tumor DNA previously determined to contain mutations in a tumor-associated gene, p16 (Kamb et al., 1994, *Proc. Natl. Acad. Sci. USA* 89: 10557–10561) is used to prepared specific amplified fragments, preferably produced using the polymerase chain reaction (see Saiki et al, 1985, Science 230: 1350). These fragments are isolated and cloned using conventional techniques (see Sambrook et al., 1990, *Molecular Cloning: A Laboratory Manual*, Cold Spring Harbor Laboratory Press: Cold Spring Harbor, N.Y.). As shown in FIG. 2B, a series of five experiments were performed. In the first three sets of experiments (described in Example 1), CMC modification was used to detect an 18 bp deletion specifically found in fragments derived from squamous cell carcinoma DNA. In the second two sets of experiments (described below in Example 2) CMC modification was used to detect an 1 bp deletion specifically found in fragments derived from squamous cell carcinoma DNA. The fragments used in heteroduplex formation reactions in these described experiments are shown in FIG. 2C. Heteroduplexes were formed using either a purified, p16-specific 192 bp fragment (experiments 1.1), a mixture of a restriction enzyme digestion comprising the 192 bp fragment and two fragments derived from plasmid DNA (experiments 1.2), or linearized plasmid containing the p16 specific fragment (experiments 1.3), wherein the corresponding mutant fragments contained the 18 bp deletion. Heteroduplexes were also formed using either a mixture of a restriction enzyme digestion comprising a 302 bp, p16-specific fragment and a fragment derived from plasmid DNA (experiments 2.1), or linearized plasmid containing the p16 specific fragment (experiments 2.2), wherein the corresponding mutant fragments contained the 1 bp deletion.

The Examples which follow are illustrative of specific embodiments of the invention, and various uses thereof. They set forth for explanatory purposes only, and are not to be taken as limiting the invention.

EXAMPLE 1

Detection of 18 Basepair Deletion in Human p16 Tumor Suppressor Gene

1. Using Cloned Purified PCR Fragments

The methods of the invention were used to detect an 18 basepair (bp) deletion in a human tumor suppressor gene found in a human tumor sample. A tumor sample and matched normal tissue from a human patient (#63) having a squamous cell carcinoma of the head and neck was obtained from the Tissue Procurement Service at the Ohio State University. DNA was extracted from the tumor (63T) and normal (63N) tissue using the Trizol DNA Extraction Kit (Life Technologies, Gaithersburg, MD) according to the manufacturer's instructions.

The tumor suppressor gene p16 is known to be involved in tumorigenesis in squamous cell carcinomas of the head and neck (Kamb et al., 1994, *Proc. Natl. Acad. Sci. USA* 89: 10557–10561; Weghorst et al., 1996, *Cancer Res.* 37: 582; Chen et al., 1996, *Carcinogenesis* 17: 2603–2607). p16 tumor suppressor gene-specific fragments known to comprise an 18 bp deletion in the tumor sample were produced using 63T and 63N DNA by polymerase chain reaction (PCR). Optimized PCR reactions were performed using p16 exon 2-specific primers as follows:

CMW48 5'-ACAAGCTTCCTTTCCG
TCATGCCG-3' (sense; SEQ ID No. 1), and

CMW49 5'-CCAGGCATCGCGCAC
GTCCA-3' (antisense; SEQ ID No. 2).

A 243 bp fragment was expected to be produced from normal (wild type) human DNA (63N), while this 243 bp fragment as well as a fragment having an 18 bp deletion (therefore producing a band of 225 bp) were expected from tumor DNA (63T). PCR reactions were performed using a temperature cycling protocol of 94° C. for 1 minute, followed by 35 cycles of 92° C. for 50 seconds, 60° C. for 50 sec, and 72° C. for 50 seconds, and a final incubation of 72° C. for 7 minutes. Production of the expected 243 bp fragment from normal human DNA was verified by agarose gel electrophoresis (Sambrook et al., 1990, *Molecular Cloning: A Laboratory Manual*, Cold Spring Harbor Laboratory Press: Cold Spring Harbor, N.Y.). The existence of the expected 18 bp deletion in the PCR fragment derived from the tumor sample (63T) was verified by a modification of single-strand conformation polymorphisms analysis (SSCP; Hongyo et al., 1993, *Nucleic Acids Res.* 16: 3637–3642; Wang et al., 1996, *Carcinogenesis* 17: 625–630) and nucleic sequence analysis (Sambrook et al., ibid.). PCR fragments were purified from the reaction mixture by 2% agarose gel electrophoresis in 89 mM Tris-HCl/89 mM borate/2 mM ethylenediamine tetraacetic acid (1X Tris/Borate/EDTA buffer), band excision and DNA extraction using a kit obtained from Qiagen (Santa Clara, Calif.).

PCR fragments from normal (63N) and tumor (63T) samples were cloned into a plasmid vector (pBluescript KSII+, Stratagene, LaJolla, Calif.) as follows. The PCR fragments (200–500 ng) were made blunt ended using 1 μL (10U) of Klenow fragment of DNA polymerase I (Boehringer Mannheim, Indianapolis, Ind.) in a reaction mixture containing 10 mM apiece of dATP, dGTP, dCTP and dTTP and in a buffer supplied by the manufacturer, and incubated for 1 hour at 37° C. DNA was purified by phenol:chloroform:isoamyl alcohol (25:24:1) extraction and ethanol precipitation. Purified DNA was resuspended in 10 μL sterile, ultrapure water and ligated into pBluescript that was linearized using EcoRV restriction endonuclease (Life Technologies). The ligation reaction mixture (10 μL) was constructed by combining 6 μL PCR fragment DNA and 1 μL linearized plasmid DNA, in the presence 1U of DNA ligase (Life Technologies), in ligation buffer comprising 25 mM Tris-HCl (pH 7.6), 5 mM $MgCl_2$, 0.5 mM ATP, 0.5 mM dithiothreitol and 2.5% polyethylene glycol (PEG 8000), obtained from the manufacturer. The ligation reaction mixture was incubated overnight at 16° C.

Bacterial cultures were transformed with the products of this ligation mixture as follows. Fifty μL of transformation-competent *E. coli* (strain DH5α; Life Technologies) were transformed according to manufacturer's instructions with 2 μL of the above ligation mixture for each of the 243 bp and 225 bp PCR fragments. Transformed cells were plated on agar plates prepared with Luria/Bertani (LB) broth (Life Technologies) containing 50 μg/mL ampicillin and spread with 40 μL of a solution of 20 mg/mL 5-bromo-4-chloro-3-indolyl-β-D-galactoside in dimethyl sulfoxide and 4 μL of a solution of 200 mg/mL isopropylthio-5-bromo-4-chloro-3-indolyl-β-D-galactoside. Bacteria were incubated at 37° C. overnight, and white bacterial colonies picked from the bacterial plate and incubated in LB broth supplemented with 50 μg/mL ampicillin to obtain sufficient bacteria to isolate plasmid DNA.

Small scale preparations of plasmid DNA were obtained using standard techniques (Sambrook et al., ibid.) and were used to verify the presence, size and orientation of the PCR fragment inserts in the cloned plasmid DNA. Large scale preparations of plasmid DNA were obtained using a Qiagen Plasmid Maxi kit according to the manufacturer's instructions.

These plasmid preparations were used to prepare restriction enzyme digested DNA. One μg of cloned plasmid DNA containing each of the two PCR fragments (63T being 225 bp in length and 63N being 243 bp in length) was digested with 10 Units apiece of the restriction enzymes SmaI and HincII (Life Technologies) at 37° C. for 4 hours. These digestions produced digestion fragments of 192, 72 and 2940 bp from plasmid containing the 63N insert, and digestion fragments of 174, 72 and 2940 bp from plasmid containing the 63T insert. Preparative gel electrophoresis was performed on the digested plasmid DNA as follows. The digested DNAs were mixed with loading dye (0.25% bromophenol blue, 0.25% xylene cyanol FF and 15% Ficoll) and separated by 1.8% agarose gel electrophoresis in TBE buffer at 120 V. Also separated in individual lanes on each gel were 100 bp DNA ladder fragments (Life Technologies) and samples of the digestion mixture to facilitate accurate visualization of the DNA fragments in the preparative lanes. After electrophoresis, the gels were stained with ethidium bromide, visualized by ultraviolet transillumination and photographed. The reference lanes were cut from the preparative gel and the appropriate bands (192 bp from cloned 63N DNA and 174 bp from 63T DNA) excised from the gel. The DNA fragments were purified from the gel using a Qiagen Gel Extraction kit according to the manufacturer's instructions and the DNA resuspended in sterile, deionized/distilled water.

Heteroduplex DNA was prepared from the purified DNA fragments as follows. Forty μL of the 192 bp fragment from 63N DNA were combined with 14 μL of the 174 bp fragment from 63T DNA (a 3:1 molar ratio) in a 650 μL plastic centrifuge tube. The total amount of DNA present in this mixture was estimated to be about 200 ng. To this DNA fragment mixture was added 10 μL of hybridization buffer (1M NaCl/100 mM MgCl$_2$/1M Na Borate, pH 8) and distilled water to a final volume of 100 μL. The samples were then heated to 100° C. for 5 minutes and allowed to renature at 42° C. overnight. After overnight incubation, the hybridization mixtures were placed at room temperature for an additional 10 minutes. Homoduplex DNA was prepared using the same method except that only 63N DNA (54 μL total) was added to the hybridization mixture.

Single-stranded DNA that did not reanneal during the hybridization incubation was eliminated by exonuclease digestion. To 60 μL of each hybridization mixture was added 34.2 μL of 100 mM borate buffer (pH 8), 0.8 μL 500 mM MgCl$_2$ and 5 μL (100U) exonuclease I (Epicentre Technologies, Madison, Wis.) and the reaction incubated at 37° C. for 1 hour. In control reactions, exonuclease I digestion of heteroduplex DNA was not performed.

Heteroduplex DNA was modified with N-cyclohexyl-N'-(2-morpholinoethyl)-carbodiimide-methyl-p-toluenesulfonate (CMC) as follows. A 400 mM CMC solution was prepared immediately before use by dissolving 168 mg CMC (Fluka Chemical, Switzerland) in 1 mL water. Twenty-five μL of the CMC solution were added to 100 μL of the heteroduplex DNA/homoduplex DNA mixture described above and incubated at 30° C., 45° C., 50° C. or 55° C. for 1 hour. Homoduplex-containing control samples were reacted with CMC as described at 30° C. The DNA was then mixed with gel loading buffers and electrophoresed at 250V for about 1.5 hours on a 20% denaturing polyacrylamide gel obtained from NOVEX (San Diego, Calif.) containing lanes including 100 bp ladder DNA for relative size determinations. After electrophoresis, gels were stained with ethidium bromide for 5 minutes, destained in distilled water for 10 minutes and photographed.

CMC-modified heteroduplex DNA mismatches were detected immunochemically as follows. Gels were immersed in TBE solution and then DNA was transferred to a nitrocellulose filter (Schleicher & Schuell, Keane, N.H.) using a NOVEX gel transfer apparatus at 25V for 1.5 hours. After transfer, the DNA was crosslinked to the nitrocellulose filter using a UV Stratalinker 1800 (Stratagene) for 40 seconds using the "auto crosslink" setting. The filter was then prehybridized by placing the filter in a heat-sealed bag containing "1BLOTTO" solution (5% Carnation non-fat dry milk/20 mM Tris-HCl, pH 8/120 mM glycine/0.8% Tween-20/0.02% Antifoam A/0.02% sodium azide) and incubating the filter overnight at 37° C. with gentle rocking/agitation. (The reagents used in preparing BLOTTO solution were obtained from Sigma Chemical Co., St. Louis, Mo.). After incubation, the BLOTTO solution was removed from the filter and replaced with 10 mL CMC primary rabbit antibody (Wani et al., 1989, Nucleic Acids Res. 17: 9957–9977; Wani & Yamasaki, 1991, Biochem Biophys. Acta 1088: 259–269) at a final dilution of 1:2000 in fresh BLOTTO solution. The filter was incubated in the presence of the CMC primary antibody at 37° C. for 1 hour with gentle rocking/agitation. After incubation, the primary rabbit antibody solution was removed from the filter and the filter washed once with a solution of phosphate buffered saline, pH 7.3/0.1 % Tween 20, followed by one washing with a solution of phosphate buffered saline, pH 7.3/0.1 % Tween 20/0.5 M NaCl and then again washed once with a solution of phosphate buffered saline, pH 7.3/0.1 % Tween 20. After the last wash, the wash solution was removed from the filter and replaced with 10 mL secondary goat anti-rabbit antibody conjugated with alkaline phosphatase (GARI-AP, Boehringer Mannheim) at a final dilution of 1:2000 in fresh BLOTTO solution. The filter was incubated in the presence of the secondary goat anti-rabbit antibody at 37° C. for 1 hour with gentle rocking/agitation. After incubation, the secondary goat anti-rabbit antibody solution was removed from the filter and the filter washed once with a solution of phosphate buffered saline, pH 7.3/0.1% Tween 20, followed by one washing with a solution of phosphate buffered saline, pH 7.3/0.1% Tween 20/0.5 M NaCl and then once again washed once with a solution of phosphate buffered saline, pH 7.3/0.1 % Tween 20. The filter was then washed in a solution of 100 mM Tris-HCl, pH 9.5/100 mM NaCl/2 mM MgCl$_2$ (AP 9.5 buffer). The filter was transferred to a fresh heat sealed bag and then washed with 20 mL of AP 9.5 buffer. Immediately prior to performing the assay, 100 μL each of a solution of nitro-blue tetrazolium (NBT: 66 mg/mL in 70% dimethylformamide) and a solution of 5-bromo-4-chloro-3-indole phosphate (BCIP: 34 mg/mL in 70% dimethylformamide) were added to 10 mL AP 9.5 buffer. (The reagents used in preparing this solution were obtained from Sigma Chemical Co.) The AP 9.5 buffer wash was removed from the filter and the NBT/BCIP containing AP 9.5 buffer was added to the filter in the heat sealed bag and incubated for 20–120 minutes in the dark. The reaction was stopped by removing the filter from the bag and washing the filter in cold water.

Figure 3:
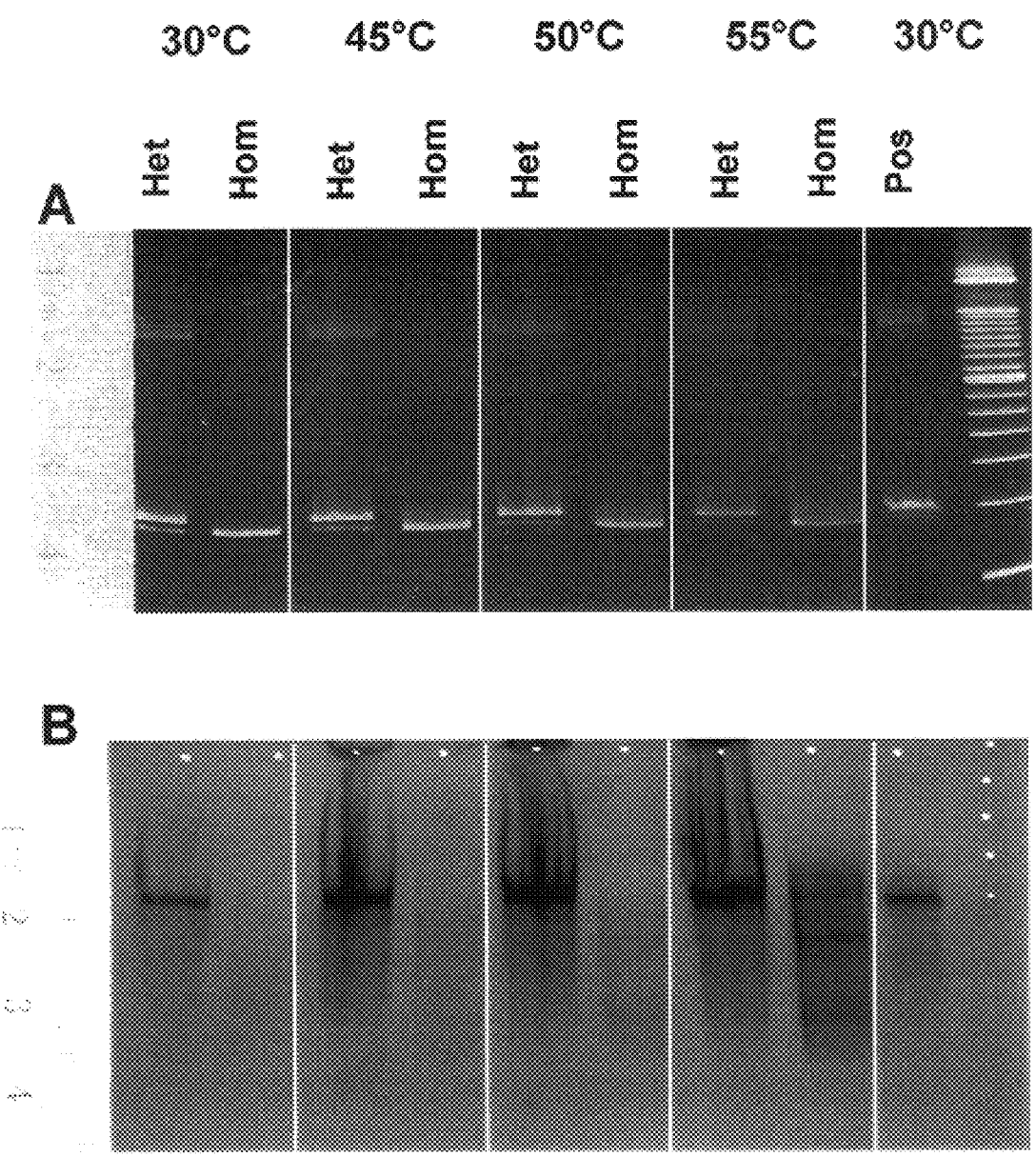
FIG. 3A depicts an ethidium bromide stained polyacrylamide gel and FIG. 3B is a photograph of a immunochemically stained nitrocellulose filter, each containing heteroduplexes and homoduplexes prepared as described in Example 1.1.

The results of these experiments are shown in FIGS. 3A and 3B. The Figure shows a photograph of the ethidium bromide-stained acrylamide gel (FIG. 3A) and the alkaline phosphatase-stained nitrocellulose filter (FIG. 3B). The identities of the DNA samples contained in each lane of the gel and filter is shown in Table I as follows:

TABLE I

| Lane # | CMC Incubation Temp. | Samples |
| --- | --- | --- |
| 1 | 30° C. | Heteroduplex 63T/N |
| 2 | 30° C. | Homoduplex 63N |
| 3 | 45° C. | Heteroduplex 63T/N |
| 4 | 45° C. | Homoduplex 63N |
| 5 | 50° C. | Heteroduplex 63T/N |
| 6 | 50° C. | Homoduplex 63N |
| 7 | 55° C. | Heteroduplex 63T/N |
| 8 | 55° C. | Homoduplex 63N |
| 9 | 30° C. | Heteroduplex 63T/N (without Exonuclease I) |
| 10 | | 100 bp DNA ladder |

The results shown in FIG. 3B demonstrated specific detection of a clearly differentiated band representing the heteroduplex fragment containing an 18 bp mismatch that was seen in each heteroduplex-containing lane at each temperature at which CMC modification was performed. The results seen in the homoduplex lanes showed no detection of DNA mismatches for homoduplexes reacted with CMC at 30° C., 45° or 50° C.; non-specific staining was seen for multiple bands in lanes representing homoduplex DNA modified with CMC at 55° C. In the positive control lane, a strong band was seen even at CMC modifications performed at 30° C., illustrating the importance of exonuclease I treatment of homoduplex (and presumable heteroduplex) mixtures for avoiding artifactual visualization of single stranded (but not mismatched) DNA. These results demonstrated that the methods of the invention were capable of detecting an 18 bp mismatch in heteroduplex DNA under conditions of essentially no detectable background.

2. Using a Restriction Enzyme Digestion Mixture of Cloned PCR Fragments

Heteroduplex analysis on cloned PCR fragments of the tumor suppressor gene p16 produced by PCR amplification of tumor (63T) and paired normal (63N) tissue DNA from a squamous cell carcinoma patient as described above in Example 1.1 was repeated under conditions where heteroduplex and homoduplex formation was performed using the complete restriction enzyme digestion mixture rather than the isolated 192 bp and 174 bp fragments. In these experiments, SmaI and HincII restriction enzyme digestion of cloned normal (243 bp) and tumor-derived (225 bp) fragments were used to prepare homoduplexes and heteroduplexes as follows. Heteroduplex DNA was prepared by mixing 50 μL of 63N DNA and 30 μL of 63T DNA (a 3:1 molar ratio) in a plastic 650 μL microcentrifuge tube. To this DNA fragment mixture was added 10 μL of hybridization buffer as described above and distilled water to a final volume of 100 μL. The samples were then heated to 100° C. for 5 minutes and allowed to renature at 42° C. overnight. After overnight incubation, the hybridization mixtures were placed at room temperature for an additional 10 minutes. Homoduplex DNA was prepared using the same method except that only 63N DNA (80 μL total) was added to the hybridization mixture.

In these experiments, the heteroduplex mixtures contained restriction enzyme digestion fragments from 63T DNA (174 bp, 72 bp and 2940 bp) and 63N DNA (192 bp, 72 bp and 2940 bp); homoduplex mixtures contain only the 63N DNA fragments. These heteroduplex and homoduplex mixtures were CMC modified, separated by gel electrophoresis, transferred to nitrocellulose, hybridized with CMC-specific antibodies and stained with alkaline phosphatase-conjugated secondary antibody as described above.

Figure 4:
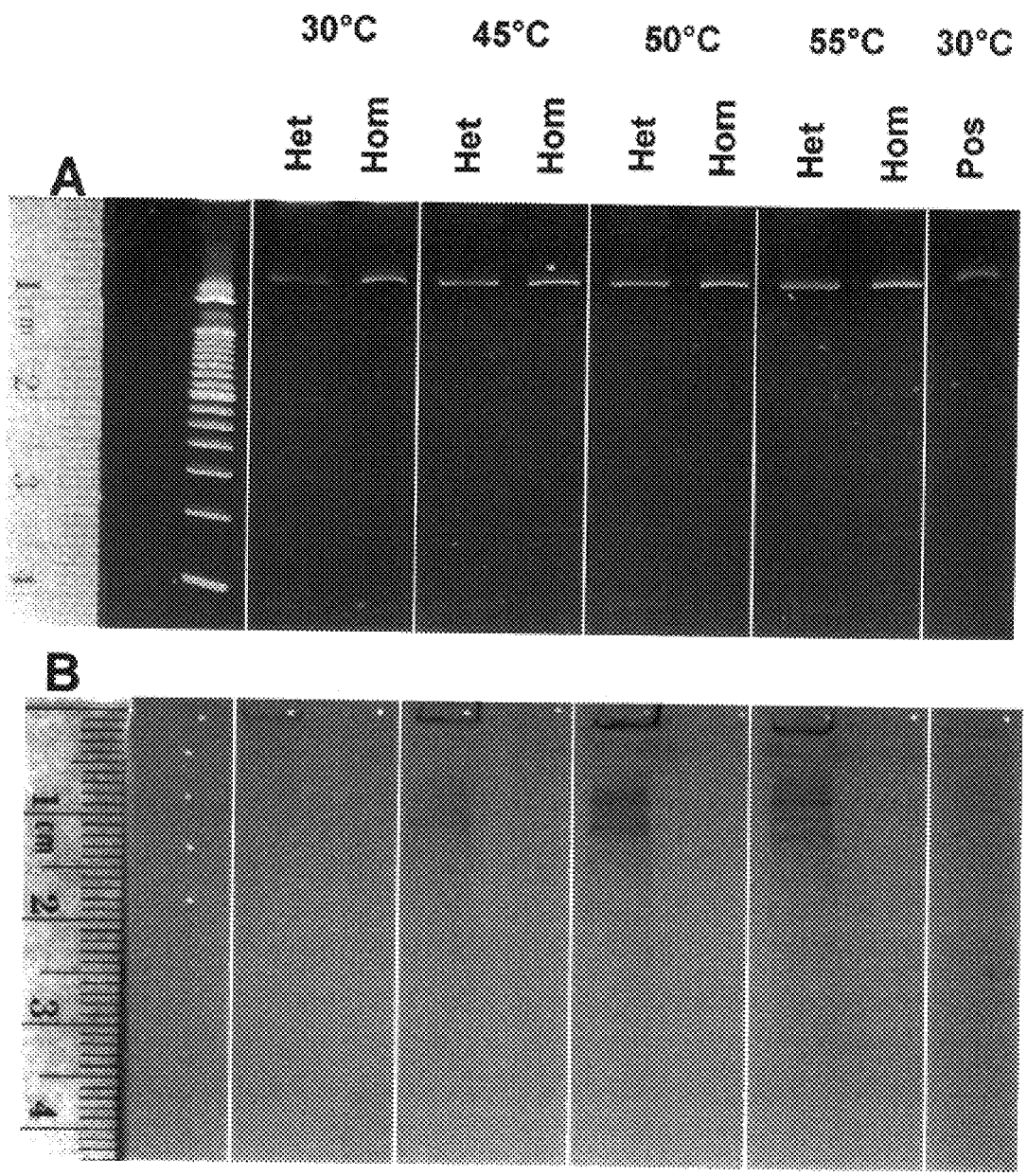
FIG. 4A depicts an ethidium bromide stained polyacrylamide gel and FIG. 4B is a photograph of a immunochemically stained nitrocellulose filter, each containing heteroduplexes and homoduplexes prepared as described in Example 1.2.

The results of these experiments are shown in FIGS. 4A and 4B. The Figure shows a photograph of the ethidium bromide-stained acrylamide gel (FIG. 4A) and the alkaline phosphatase-stained nitrocellulose filter (FIG. 4B). The identities of the DNA samples contained in each lane of the gel and filter is shown in Table II as follows:

TABLE II

| Lane # | CMC Incubation Temp. | Samples |
| --- | --- | --- |
| 1 |  | 100 bp DNA Ladder |
| 2 | 30° C. | Heteroduplex 63T/N |
| 3 | 30° C. | Homoduplex 63N |
| 4 | 45° C. | Heteroduplex 63T/N |
| 5 | 45° C. | Homoduplex 63N |
| 6 | 50° C. | Heteroduplex 63T/N |
| 7 | 50° C. | Homoduplex 63N |
| 8 | 55° C. | Heteroduplex 63T/N |
| 9 | 55° C. | Homoduplex 63T/N |
| 10 | 30° C. | Heteroduplex 63T/N (without Exonuclease I) |

The results shown in FIG. 4B demonstrated specific detection of clearly differentiated bands representing the heteroduplex fragment containing an 18 bp mismatch that was seen in each lane containing heteroduplex DNA at all temperatures at which CMC modification was performed. The results seen in the homoduplex lanes showed no detection of DNA mismatches for homoduplexes reacted with CMC at any temperature. In the positive control lane, a broad smear of staining comprising multiple bands was seen even at CMC modifications performed at 30° C., illustrating the importance of exonuclease I treatment of homoduplex (and presumable heteroduplex) mixtures for avoiding artifactual visualization of single stranded (but not mismatched) DNA. These results demonstrated that the methods of the invention were capable of detecting an 18 bp mismatch in heteroduplex DNA under conditions of essentially no detectable background even in the presence of a vast excess of non-specific plasmid DNA.

3. Using Linearized Plasmid Clones of PCR Fragments

Heteroduplex analysis on cloned PCR fragments of the tumor suppressor gene p16 produced by PCR amplification of tumor (63T) and paired normal (63N) tissue DNA from as squamous cell carcinoma patient as described above in Example 1.1 was repeated under conditions where heteroduplex and homoduplex formation was performed using linearized plasmids containing PCR amplified DNA fragments rather than the isolated 192 bp and 174 bp fragments described in Examples 1.1 and 1.2 above. In these experiments, 1 μg plasmid DNA containing normal (243 bp) and tumor-derived (225 bp) PCR fragments were digested with HincII. Linearized plasmid DNAs were used to prepare homoduplexes and heteroduplexes as follows. Heteroduplex DNA was prepared by mixing 50 μL of 63N DNA and 30 μL of 63T DNA (a 3:1 molar ratio) in a plastic 650 μL microcentrifuge tube. To this DNA fragment mixture was added 10 μL of hybridization buffer as described above and distilled water to a fmal volume of 100 μL. The samples were then heated to 100° C. for 5 minutes and allowed to renature at 42° C. overnight. After overnight incubation, the hybridization mixtures were placed at room temperature for an additional 10 minutes. Homoduplex DNA was prepared using the same method except that only 63N DNA (80 μL total) was added to the hybridization mixture.

In these experiments, the heteroduplex mixtures contained a 3186 bp linearized plasmid from 63T DNA and 3204 bp linearized plasmid from 63N DNA; homoduplex mixtures contained only the 3204 bp linearized 63N DNA containing plasmid. These heteroduplex and homoduplex mixtures were CMC modified, separated by gel electrophoresis, transferred to nitrocellulose, hybridized with CMC-specific antibodies and stained with alkaline phosphatase-conjugated secondary antibody as described above.

Figure 5:
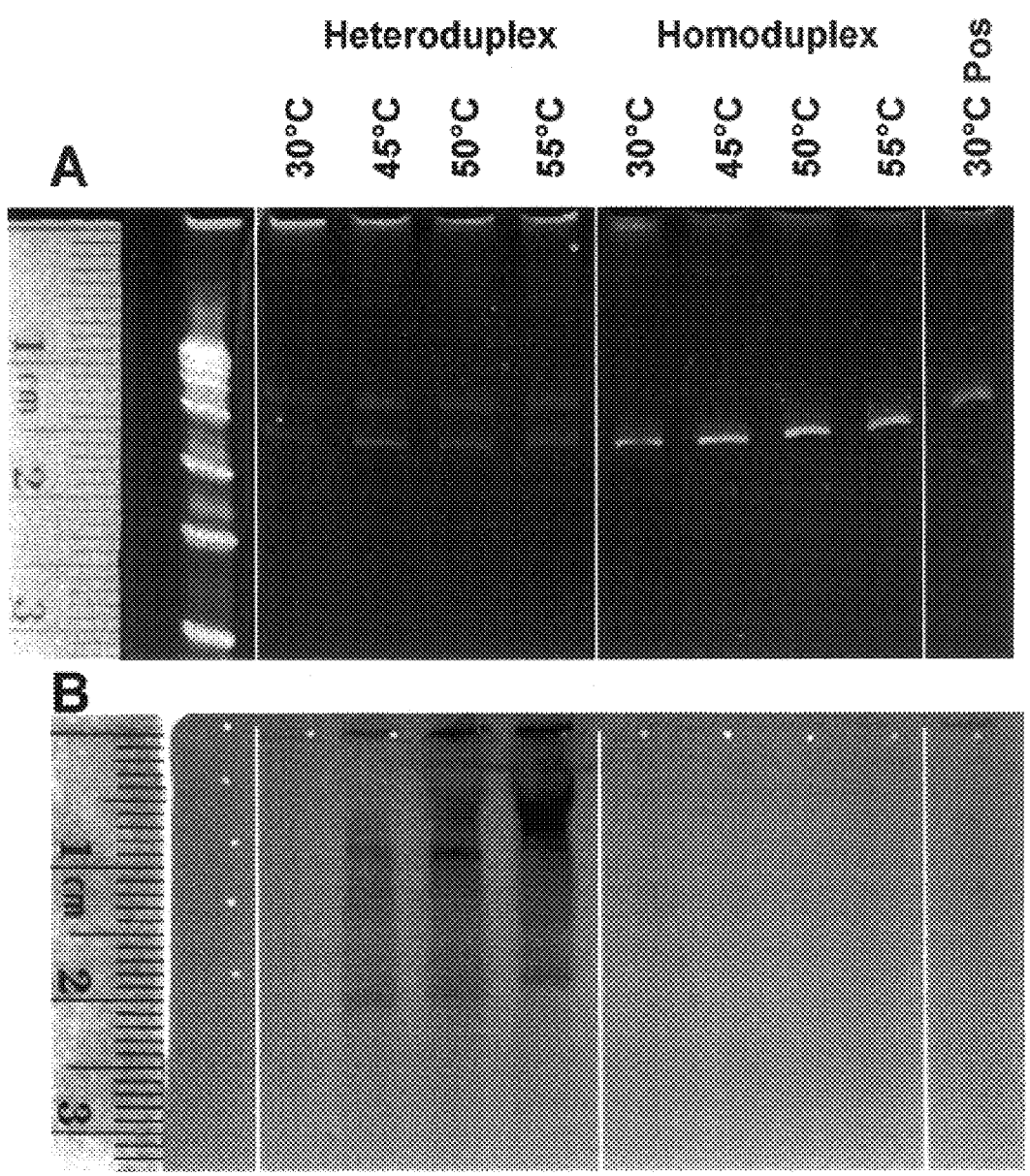
FIG. 5A depicts an ethidium bromide stained polyacrylamide gel and FIG. 5B is a photograph of a immunochemically stained nitrocellulose filter, each containing heteroduplexes and homoduplexes prepared as described in Example 1.3.

The results of these experiments are shown in FIGS. 5A and 5B. The Figure shows a photograph of the ethidium bromide-stained acrylamide gel (FIG. 5A) and the alkaline phosphatase-stained nitrocellulose filter (FIG. 5B). The identities of the DNA samples contained in each lane of the gel and filter is shown in Table III as follows:

TABLE III

| Lane # | CMC Incubation Temp. | Samples |
| --- | --- | --- |
| 1 |  | 100 bp Ladder |
| 2 | 30° C. | Heteroduplex 63T/N |
| 3 | 45° C. | Heteroduplex 63T/N |
| 4 | 50° C. | Heteroduplex 63T/N |
| 5 | 55° C. | Heteroduplex 63T/N |
| 6 | 30° C. | Homoduplex 63N |
| 7 | 45° C. | Homoduplex 63N |
| 8 | 50° C. | Homoduplex 63N |
| 9 | 55° C. | Homoduplex 63N |
| 10 | 30° C. | Heteroduplex 63T/N (without Exonuclease I) |

The results shown in FIG. 5B demonstrated specific detection of clearly differentiated bands representing the heteroduplex fragment containing an 18 bp mismatch that was seen in lanes containing heteroduplex DNA representing CMC modification temperatures of 45° C., 50° C. and 55° C.; no bands were detected for CMC modification performed at 30° C. The results seen in the homoduplex lanes showed no detection of DNA mismatches for homoduplexes reacted with CMC at any temperature. Even in the positive control lane, no staining was detected at CMC modifications performed at 30° C. These results indicated that excess single stranded DNA was not present in these hybridizations, or that specific species were not present in sufficient concentration to be detected as a band on the nitrocellulose filter. These results demonstrated that the methods of the invention were capable of detecting an 18 bp mismatch in heteroduplex DNA under conditions of essentially no detectable background even in the presence of a vast excess of non-specific plasmid DNA that is covalently linked and physically conjugated to the mismatch-containing DNA.

EXAMPLE 2
Detection of 1 Basepair Mismatch in Human p16 Tumor Suppressor Gene

1. Using a Restriction Enzyme Digestion Mixture of Cloned PCR Fragments

A tumor sample and matched normal tissue from a human patient (#135) having a squamous cell carcinoma of the head and neck was obtained from the Tissue Procurement Service at the Ohio State University. DNA was extracted from the tumor (135T) and normal (135N) tissue as described in Example 1 above.

Optimized PCR amplification of p16 exon 2-specific DNA fragments were performed for normal and tumor DNA as described in Example 1, using the following PCR primers:

CMW50 5'-TTCCTGGACACGCTGG
       TGGT-3'                (sense; SEQ ID No. 3), and CMW51 5'-TCTGAGCTTTGGAAGC
       TCTCAG-3'              (antisense; SEQ ID No. 4).

A 242 bp fragment was expected to be produced from normal (wild type) human DNA (135N), while both this 242 bp fragment and a fragment having a 1 bp deletion (therefore producing a 241 bp fragment) were expected from tumor DNA (135T). PCR reactions were performed using the temperature cycling protocol described in Example 1. Production of the expected 242 bp fragment from normal human DNA was verified by agarose gel electrophoresis (Sambrook et al., ibid.). The existence of the expected 1 bp deletion mutation in the PCR fragment derived from the tumor sample (135T) was verified a modification of SSCP analysis as described in Example 1 above. PCR fragments were purified from the reaction mixture by 2% agarose gel electrophoresis and DNA extraction as described above in Example 1.

PCR fragments from normal (135N) and tumor (135T) samples were cloned into a plasmid vector (pBluescript KSII+, Stratagene, LaJolla, Calif.) as described in Example 1, and 1 µg of each isolated plasmid digested with SmaI and HincII as described above. This digestions produced DNA fragments of 302 bp and 2901 bp from plasmid containing PCR fragments produced from normal DNA (135N) and DNA fragments of 301 bp and 2901 bp from plasmid containing PCR fragments produced from normal DNA (135T).

Heteroduplex analysis was performed as described above in Example 1 using the complete restriction enzyme digestion mixture. Heteroduplex DNA was prepared by mixing 65 µL of 135N DNA and 15 µL of 135T DNA (a 3:1 molar ratio) in a plastic 650 µL microcentrifuge tube. To this DNA fragment mixture was added 10 µL of hybridization buffer as described above and distilled water to a final volume of 100 µL. The samples were then heated to 100° C. for 5 minutes and allowed to renature at 42° C. overnight. After overnight incubation, the hybridization mixtures were placed at room temperature for an additional 10 minutes. Homoduplex DNA was prepared using the same method except that only 135N DNA (80 µL total) was added to the hybridization mixture.

In these experiments, the heteroduplex mixtures contained digestion fragments from 135T DNA (301 bp and 2901 bp) and 135N DNA (302 bp and 2901 bp); homoduplex mixtures contain only the 135N DNA fragments. These heteroduplex and homoduplex mixtures were CMC modified, separated by gel electrophoresis, transferred to nitrocellulose, hybridized with CMC-specific antibodies and stained with alkaline phosphatase-conjugated secondary antibody as described above.

Figure 6:
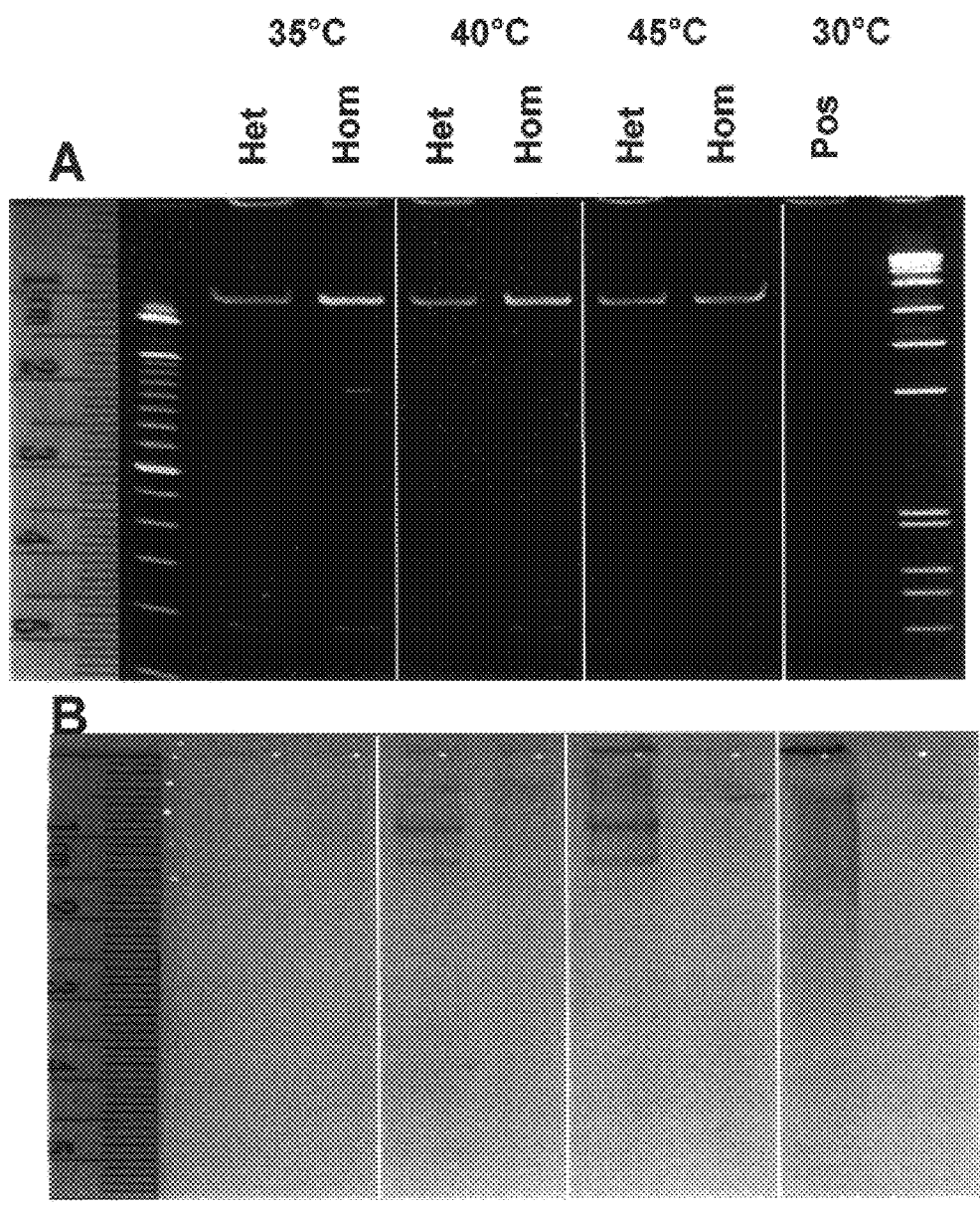
FIG. 6A depicts an ethidium bromide stained polyacrylamide gel and FIG. 6B is a photograph of a immunochemically stained nitrocellulose filter, each containing heteroduplexes and homoduplexes prepared as described in Example 2.1.

The results of these experiments are shown in FIGS. 6A and 6B. The Figure shows a photograph of the ethidium bromide-stained acrylamide gel (FIG. 6A) and the alkaline phosphatase-stained nitrocellulose filter (FIG. 6B). The identities of the DNA samples contained in each lane of the gel and filter is shown in Table IV as follows:

TABLE IV

| Lane # | CMC Incubation Temp. | Samples |
| --- | --- | --- |
| 1 | | 100 bp DNA Ladder |
| 2 | 35° C. | Heteroduplex 135T/N |
| 3 | 35° C. | Homoduplex 135N |
| 4 | 40° C. | Heteroduplex 135T/N |
| 5 | 40° C. | Homoduplex 135N |
| 6 | 45° C. | Heteroduplex 135T/N |
| 7 | 45° C. | Homoduplex 135N |
| 8 | 30° C. | Heteroduplex 135T/N (without Exonuclease I) |
| 9 | | 100 bp DNA Ladder |

The results shown in FIG. 6B demonstrated specific detection of clearly differentiated bands representing the heteroduplex fragment containing an 1 bp mismatch that was seen in lanes containing heteroduplex DNA representing CMC modification temperatures of 40° C. and 45° C.; no specific bands were detected for CMC modification performed at 30° C. The results seen in the homoduplex lanes showed no specific bands corresponding to DNA mismatches for homoduplexes reacted with CMC at any temperature; the extend of non-specific band detection appeared independent to CMC modification temperature. In the positive control lane, a broad smear to staining comprising multiple bands was seen even at CMC modifications performed at 30° C., illustrating the importance of exonuclease I treatment of homoduplex (and presumable heteroduplex) mixtures for avoiding artifactual visualization of single stranded (but not mismatched) DNA. These results demonstrated that the methods of the invention were capable of detecting a 1 bp mismatch in heteroduplex DNA under conditions of essentially no detectable background even in the presence of a vast excess of non-specific plasmid DNA.

2. Using Linearized Plasmid Clones of PCR Fragments

Heteroduplex analysis on cloned PCR fragments of the tumor suppressor gene p16 produced by PCR amplification of tumor (135T) and paired normal (135N) tissue DNA from as squamous cell carcinoma patient as described above in Example 2.1 was repeated under conditions where heteroduplex and homoduplex formation was performed using linearized plasmids containing PCR amplified DNA fragments. In these experiments, 1 µg plasmid DNA containing normal (242 bp) and tumor-derived (241 bp) PCR fragments were digested with HincII. Linearized plasmid DNAs were used to prepare homoduplexes and heteroduplexes as follows. Heteroduplex DNA was prepared by mixing 60 μL of 135N DNA and 30 μL of 135T DNA (a 3:1 molar ratio) in a plastic 650 μL microcentrifuge tube. To this DNA fragment mixture was added 10 μL of hybridization buffer as described above and distilled water to a final volume of 100 μL. The samples were then heated to 100° C. for 5 minutes and allowed to renature at 42° C. overnight. After overnight incubation, the hybridization mixtures were placed at room temperature for an additional 10 minutes. Homoduplex DNA was prepared using the same method except that only 135N DNA (80 μL total) was added to the hybridization mixture.

In these experiments, the heteroduplex mixtures contained a 3202 bp linearized plasmid from 135T DNA and 3203 bp linearized plasmid from 135N DNA; homoduplex mixtures contained only the 3203 bp linearized 135N DNA containing plasmid. These heteroduplex and homoduplex mixtures were CMC modified, separated by gel electrophoresis, transferred to nitrocellulose, hybridized with CMC-specific antibodies and stained with alkaline phosphatase-conjugated secondary antibody as described above.

Figure 7:
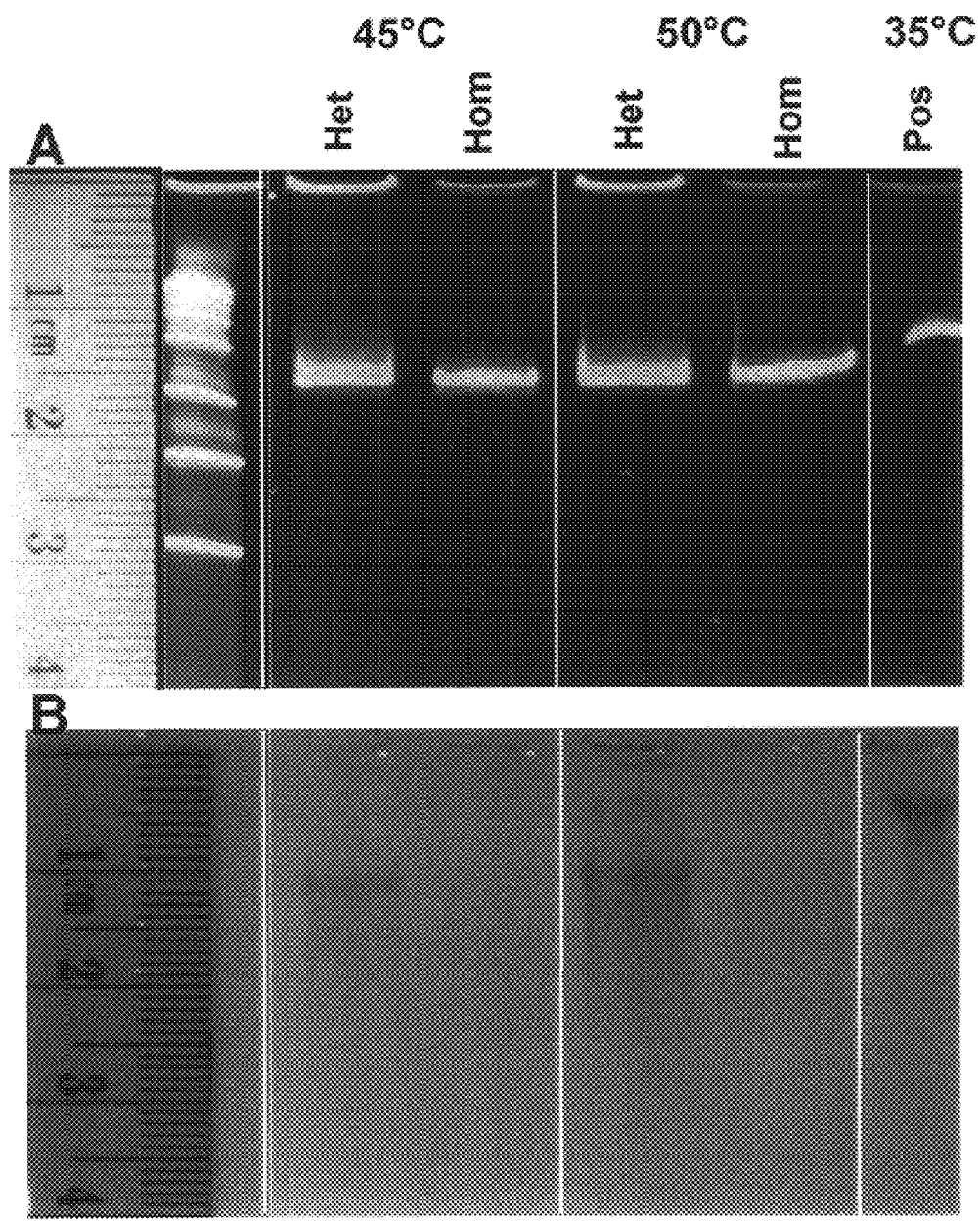
FIG. 7A depicts an ethidium bromide stained polyacrylamide gel and FIG. 7B is a photograph of a immunochemically stained nitrocellulose filter, each containing heteroduplexes and homoduplexes prepared as described in Example 2.2.

The results of these experiments are shown in FIGS. 7A and 7B. The Figure shows a photograph of the ethidium bromide-stained acrylamide gel (FIG. 7A) and the alkaline phosphatase-stained nitrocellulose filter (FIG. 7B). The identities of the DNA samples contained in each lane of the gel and filter is shown in Table V as follows:

TABLE V

| Lane # | CMC Incubation Temp. | Samples |
| --- | --- | --- |
| 1 |  | 100 bp DNA Ladder |
| 2 | 35° C. | Heteroduplex 135T/N |
| 3 | 35° C. | Homoduplex 135N |
| 4 | 40° C. | Heteroduplex 135T/N |
| 5 | 40° C. | Homoduplex 135N |
| 6 | 45° C. | Heteroduplex 135T/N |
| 7 | 45° C. | Homoduplex 135N |
| 8 | 50° C. | Heteroduplex 135T/N |
| 9 | 50° C. | Homoduplex 135N |
| 10 | 35° C. | Heteroduplex 135T/N (without Exonuclease I) |

The results shown in FIG. 7B demonstrated specific detection of clearly differentiated bands representing the heteroduplex fragment containing an 1 bp mismatch that was seen in lanes containing heteroduplex DNA representing CMC modification temperatures of 45° C. and 50° C.; no bands were detected for CMC modification performed at 35° C. or 40° C. The results seen in the homoduplex lanes showed no detection of DNA mismatches for homoduplexes reacted with CMC at any temperature; non-specific staining was observed in the lane representing CMC modification of homoduplexes at 50° C. In the positive control lane, a broad smear to staining comprising multiple bands was seen even at CMC modifications performed at 35° C., illustrating the importance of exonuclease I treatment of homoduplex (and presumable heteroduplex) mixtures for avoiding artifactual visualization of single stranded (but not mismatched) DNA. These results demonstrated that the methods of the invention were capable of detecting an 1 bp mismatch in heteroduplex DNA under conditions of essentially no detectable background even in the presence of a vast excess of non-specific plasmid DNA that is covalently linked and physically conjugated to the mismatch-containing DNA.

EXAMPLE 3

Modified ELISA Assay for Detecting Heteroduplex Mismatches

A modified enzyme-linked immunosorbent assay (ELISA) was used to demonstrate detection of mismatch-containing heteroduplexes in a format amenable to automation.

Linearized plasmid DNA containing a wildtype copy of the p16 tumor suppressor gene as described in Example 1.3. After heteroduplex formation and CMC modification as described above, 0.05–2 ng of the DNA mixture were added per well of a 96-well microtitre plate and immobilized thereto by drying overnight at 37° C. The wells were washed with PBS/Tween 20 buffer and blocked with BLOTTO solution as described for the filter embodiments described in Example 1.3. Blocked microtitre wells were the sequentially incubated with primary antibody (anti-CMC) and secondary antibody (GARI-AP) at room temperature at 37° C. After the secondary antibody mixture was removed and the wells washed with PBS/Tween solution, paranitrophenylphosphate-containing solution was added and the reacted at 37° C. in the presence of the secondary antibody-linked alkaline phosphatase. Plates were read using a BioTek EIAReader (Bio-Tek Instruments Inc., Winooski, Vt.) at 496 nm over 60 minutes and absorbance plotted as a function of DNA concentration. Control wells containing only wildtype or only mutant plasmid DNA were analyzed in parallel.

Figure 10:
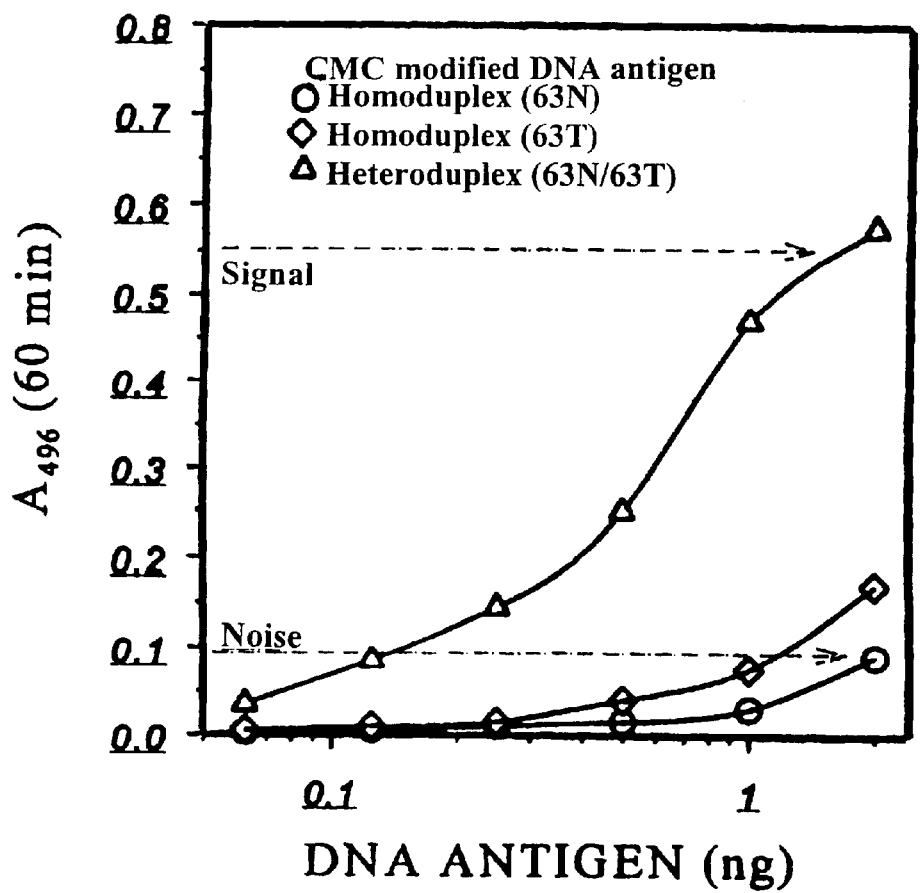
FIG. 10 shows the comparative results of enzyme-linked immunosorbent assay (ELISA) using anti-CMC antibodies and CMC-modified mismatched heteroduplex DNA as described in Example 3, wherein -◯- represents results with CMC-modified wildtype homoduplexes (63N), -◇- represent results with CMC-modified mutant homoduplexes (63T), and -△- represent results with CMC-modified heteroduplexes (63N/63T).

The results of these experiments is shown in FIG. 10. Each data point shown in the graph is an average of duplicate samples; standard deviation (2–4%) is not shown for clarity. These results demonstrated that the ELISA assay could detect mismatch-containing heteroduplexes at a signal-to-noise ratio of about 5:1. These results indicated that positive results were distinguishable from background noise and therefore that the assay was suitable for automation using commercially-available detectors.

It should be understood that the foregoing disclosure emphasizes certain specific embodiments of the invention and that all modifications or alternatives equivalent thereto are within the spirit and scope of the invention as set forth in the appended claims.

What is claimed is:

1. A method for detecting a nucleotide sequence mismatch in a heteroduplex nucleic acid molecule, the method comprising the following steps:
   a) preparing a heteroduplex between a first nucleic acid fragment and a second, complementary nucleic acid fragment having a nucleotide sequence that forms at least one nucleotide sequence mismatch when annealed with the first nucleic acid fragment;
   b) treating the heteroduplex formed in subpart (a) with an exonuclease for a time and at an activity sufficient to digest single stranded DNA;
   c) chemically modifying the heteroduplex with a reagent that forms a covalent linkage to a mismatched nucleotide in the heteroduplex; and
   d) detecting the chemically modified mismatched nucleotide heteroduplex under conditions wherein chemical modification of a homoduplex is not detected.

2. The method of claim 1, wherein the heteroduplex is modified by treatment with a reagent selected from the group consisting of N-cyclohexyl-NN-(4-methylmorpholinium)-ethylcarbodiimide (CMC), osmium tetroxide, hydroxylamine, and Mut S protein.

3. The method of claim 1, wherein the chemically modified mismatched nucleotide is detected using an immunochemical reagent.

4. The method of claim 3, wherein the immunochemical reagent is an antibody that specifically binds to CMC-modified heteroduplexes.

5. The method of claim 4, wherein the antibody is a monoclonal antibody.

6. The method of claim 4 wherein the antibody comprises a polyclonal antisera.

7. The method of claim 4 5 or 6 wherein the antibody is detectably labeled.

8. The method of claim 7, wherein the antibody is conjugated with an enzymatic moiety capable of converting a substrate to a detectable product.

9. The method of claim 1, wherein the reagent is detectably-labeled.

10. The method of claim 9, wherein the reagent is labeled with a radioisotope, a fluorescent label, a chemiluminescent label, and antigenic label or a hapten label.

11. The method of claim 10, wherein antibody binding to CMC-modified heteroduplexes is detected using a detectably-labeled antibody that specifically binds to the CMC-modified heteroduplex-specific antibody.

12. The method of claim 1, wherein the heteroduplex is prepared from DNA digested with an endonuclease.

13. The method of claim 12, wherein the endonuclease is a restriction endonuclease.

14. The method of claim 1, wherein the heteroduplex is prepared from DNA fragments produced by in vitro amplification.

15. The method of claim 14, wherein the in vitro amplification reaction is polymerase chain reaction.

16. The method of claim 3, wherein the chemically modified heteroduplex is treated by gel electrophoresis and transferred to a solid support before being detected by the immunochemical reagent.

17. The method of claim 1, wherein each of steps (a) and (b) are performed in a single reaction tube.

18. The method of claim 1, wherein each of steps (a), (b) and (d) are performed in a single reaction tube.

19. A kit for performing the method of claim 1, the kit comprising:
   a) heteroduplex formation buffer;
   b) a heteroduplex modifying reagent;
   c) a blocking solution;
   d) an immunological reagent that specifically binds to chemically modified mismatched heteroduplex nucleic acid; and e) a detecting reagent for detecting specific binding of the immunological reagent to chemically modified mismatched heteroduplex nucleic acid.

20. A kit for performing the method of claim 1, the kit comprising:
   a) heteroduplex formation buffer;
   b) a heteroduplex modifying reagent;
   c) a blocking solution;
   d) an immunological reagent that specifically binds to chemically modified mismatched heteroduplex nucleic acid;
   e) a detecting reagent for detecting specific binding of the immunological reagent to chemically modified mismatched heteroduplex nucleic acid; and
   f) an exonuclease and buffer solution therefor.

21. A kit according to claim 19 or 20 wherein the heteroduplex modifying reagent is selected from the group consisting of N-cyclohexyl-N'-(4-methylmorpholinium)-ethylcarbodiimide (CMC), osmium tetroxide, hydroxylamine, and Mut S protein.

22. A method according to claim 1, wherein the heteroduplex is immobilized on a solid support.

23. The method of claim 22, wherein the nucleotide sequence mismatch is detected by enzyme-linked immunosorbent assay.

24. A method for isolating a heteroduplex nucleic acid molecule comprising a nucleotide sequence mismatch, the method comprising the following steps:
   a) preparing a heteroduplex between a first nucleic acid fragment and a second, complementary nucleic acid fragment having a nucleotide sequence that forms at least one nucleotide sequence mismatch when annealed with the first nucleic acid fragment;
   b) treating the heteroduplex formed in subpart (a) with an exonuclease for a time and at an activity sufficient to digest single stranded DNA;
   c) chemically modifying the heteroduplex with a reagent that forms a covalent linkage to a mismatched nucleotide in the heteroduplex; and
   d) isolating the chemically modified mismatched nucleotide heteroduplex under conditions wherein chemical modification of a homoduplex is not isolated.

25. The method of claim 24, wherein the heteroduplex is modified by treatment with a reagent selected from the group consisting of N-cyclohexyl-N'-(4-methylmorpholinium)-ethylcarbodiimide (CMC), osmium tetroxide, hydroxylamine, and Mut S protein.

26. The method of claim 25, wherein the chemically modified mismatched nucleotide is isolated using an immunochemical reagent.

27. The method of claim 26, wherein the immunochemical reagent is an antibody that specifically binds to CMC-modified heteroduplexes.

28. The method of claim 27, wherein the antibody is a monoclonal antibody.

29. The method of claim 26 or 27 wherein the antibody comprises a polyclonal antisera.

30. The method of claim 26, 27 or 28, wherein the antibody is conjugated with a capture, accumulation or aggregation reagent.

31. The method of claim 30, wherein the capture, accumulation or aggregation reagent is a particle or bead, a magnetic or paramagnetic particle or bead, a ferritin complex, an antigenic or hapten-conjugated particle or bead.

32. The method of claim 24, wherein the heteroduplex molecule is digested with a site-specific endonuclease.

* * * * *